United States Patent
Dejima et al.

(10) Patent No.: US 10,456,024 B2
(45) Date of Patent: Oct. 29, 2019

(54) OVERTUBE AND ENDOSCOPIC SURGICAL DEVICE

(71) Applicant: FUJIFILM Corporation, Tokyo (JP)

(72) Inventors: Takumi Dejima, Kanagawa (JP); Toshiharu Kuwae, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 324 days.

(21) Appl. No.: 15/275,475

(22) Filed: Sep. 26, 2016

(65) Prior Publication Data

US 2017/0007109 A1 Jan. 12, 2017

Related U.S. Application Data

(63) Continuation of application No. PCT/JP2015/059350, filed on Mar. 26, 2015.

(60) Provisional application No. 61/971,102, filed on Mar. 27, 2014.

(51) Int. Cl.
*A61B 1/12* (2006.01)
*A61B 1/00* (2006.01)
(Continued)

(52) U.S. Cl.
CPC .......... *A61B 1/126* (2013.01); *A61B 1/00091* (2013.01); *A61B 1/00096* (2013.01);
(Continued)

(58) Field of Classification Search
CPC . A61B 1/00135; A61B 1/00154; A61B 1/015; A61B 1/126
See application file for complete search history.

(56) References Cited

U.S. PATENT DOCUMENTS 5,575,756 A * 11/1996 Karasawa .......... A61B 1/00068
600/121
5,630,795 A * 5/1997 Kuramoto .......... A61B 1/00068
600/153

(Continued)

FOREIGN PATENT DOCUMENTS

JP H05199979 8/1993
JP H07275185 10/1995
(Continued)

OTHER PUBLICATIONS

"Written Opinion of the International Searching Authority of PCT/JP2015/059350", dated May 19, 2015, with English translation thereof, pp. 1-8.
(Continued)

*Primary Examiner* — Aaron B Fairchild
(74) *Attorney, Agent, or Firm* — JCIPRNET

(57) ABSTRACT

A distal end of an endoscope insertion passage of an overtube is provided with a fluid supply and discharge port. When an observation window of the endoscope insertion part inserted through the endoscope insertion passage is cleaned, an operator can set a distal end surface at a predetermined positioning position using a positioning mechanism, without extracting the endoscope insertion part from the endoscope insertion passage. A concave cleaning storage part that communicates with the fluid supply and discharge port is formed inside the endoscope insertion passage on the distal end side. Cleaning water is supplied from the fluid supply and discharge port to remove foreign matter from the observation window, and stored in the cleaning storage part, and then, the cleaning water stored in the cleaning storage part is suctioned from the fluid supply and discharge port.

10 Claims, 29 Drawing Sheets

(51) Int. Cl.
*A61B 1/015* (2006.01)
*A61B 17/34* (2006.01)
*A61B 90/00* (2016.01)
*A61B 17/29* (2006.01)

(52) U.S. Cl.
CPC ...... *A61B 1/00135* (2013.01); *A61B 1/00154* (2013.01); *A61B 1/015* (2013.01); *A61B 17/3421* (2013.01); *A61B 17/29* (2013.01); *A61B 2017/347* (2013.01); *A61B 2017/3447* (2013.01)

(56) References Cited

U.S. PATENT DOCUMENTS

| | | |
|---|---|---|
| 5,697,888 A | 12/1997 | Kobayashi et al. |
| 2005/0119525 A1* | 6/2005 | Takemoto .......... A61B 1/00154 600/114 |
| 2010/0010310 A1 | 1/2010 | Weisenburgh, II et al. |
| 2012/0165610 A1 | 6/2012 | Poll et al. |
| 2015/0080650 A1 | 3/2015 | Dejima et al. |

FOREIGN PATENT DOCUMENTS

| | | |
|---|---|---|
| JP | 2010017559 | 1/2010 |
| JP | 2014018563 | 2/2014 |
| WO | 2013176167 | 11/2013 |

OTHER PUBLICATIONS

"Search Report of Europe Counterpart Application", dated Feb. 22, 2017, p. 1-p. 7.

"Office Action of European Counterpart Application," dated Jan. 31, 2018, p. 1-p. 4.

"Office Action of Japan Counterpart Application" with English translation thereof, dated May 11, 2017, p. 1-p. 8.

* cited by examiner

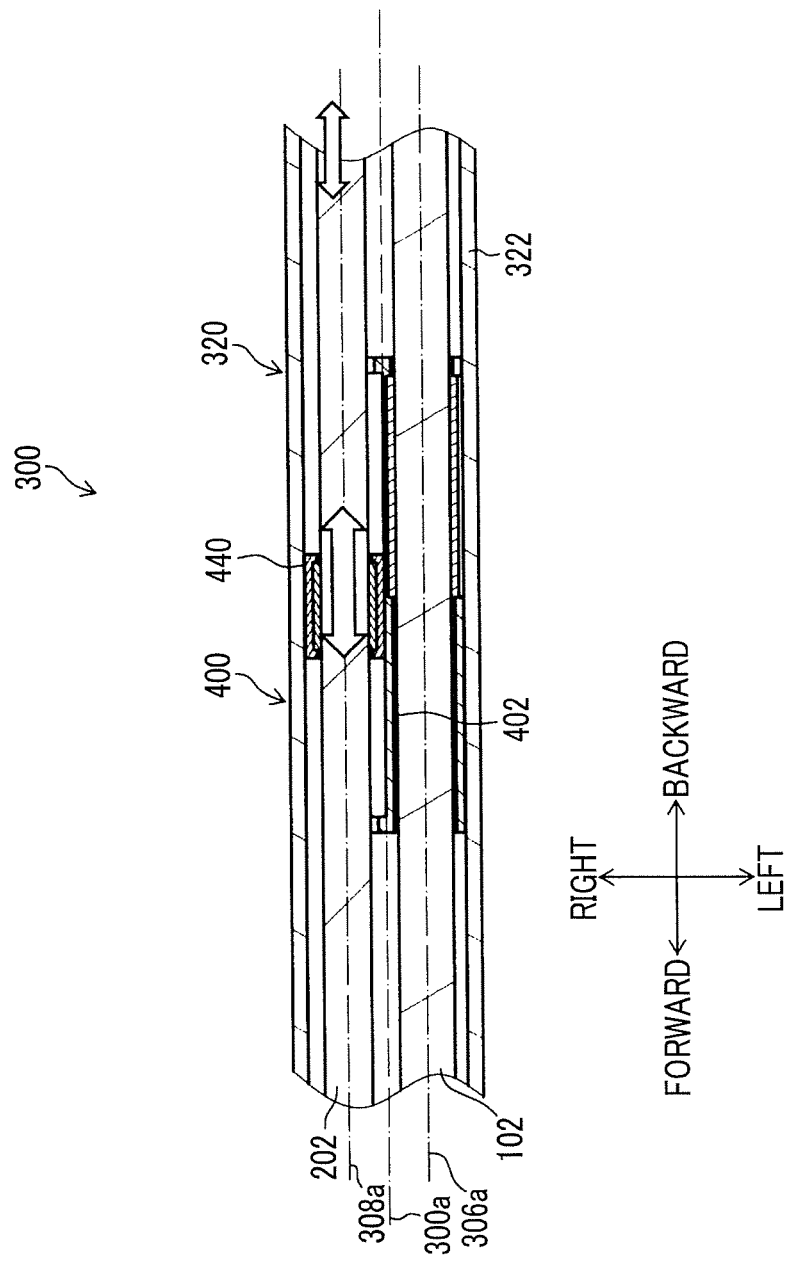

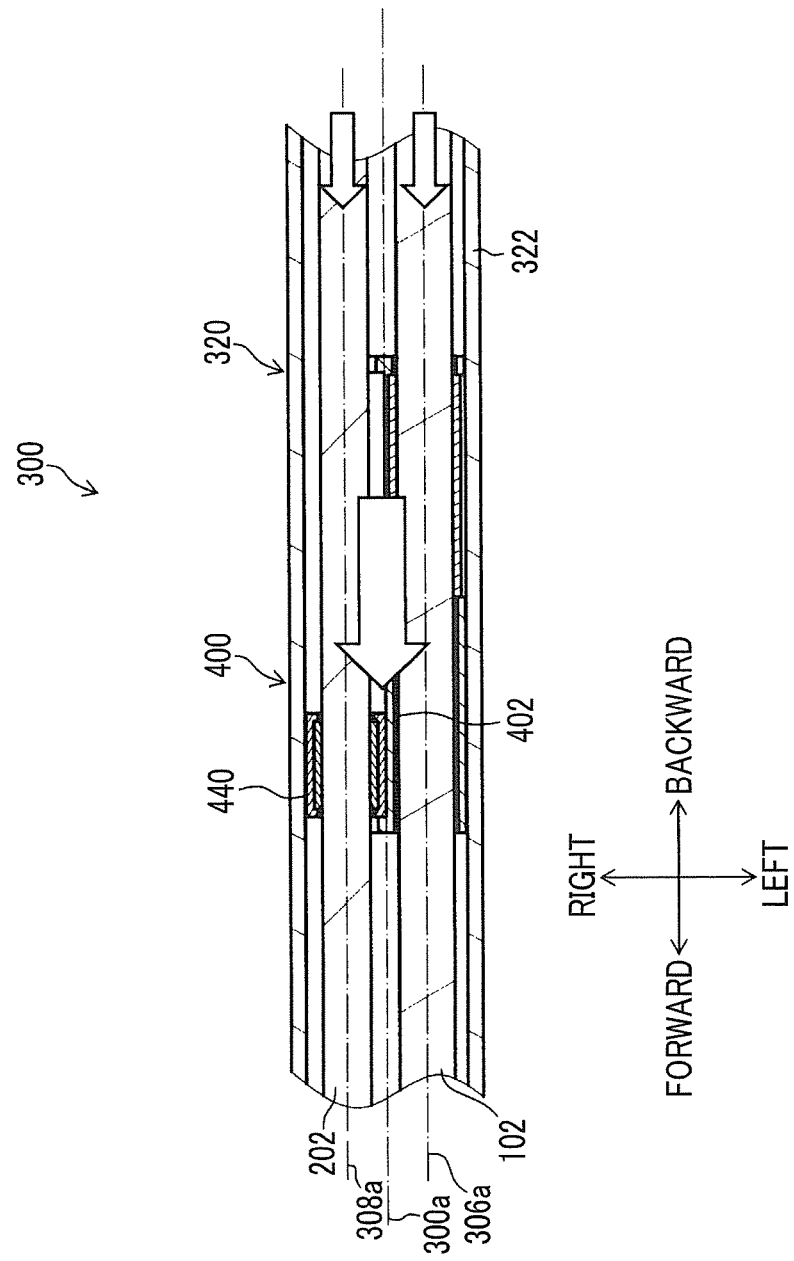

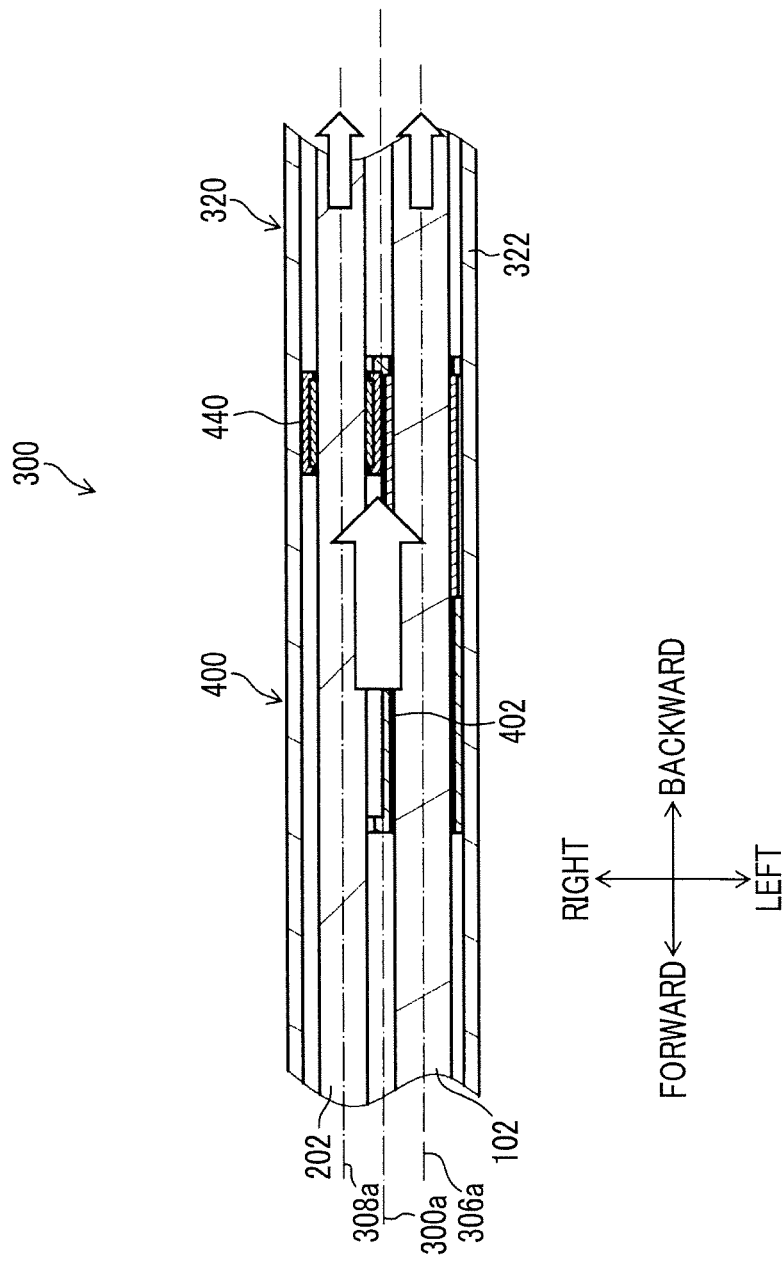

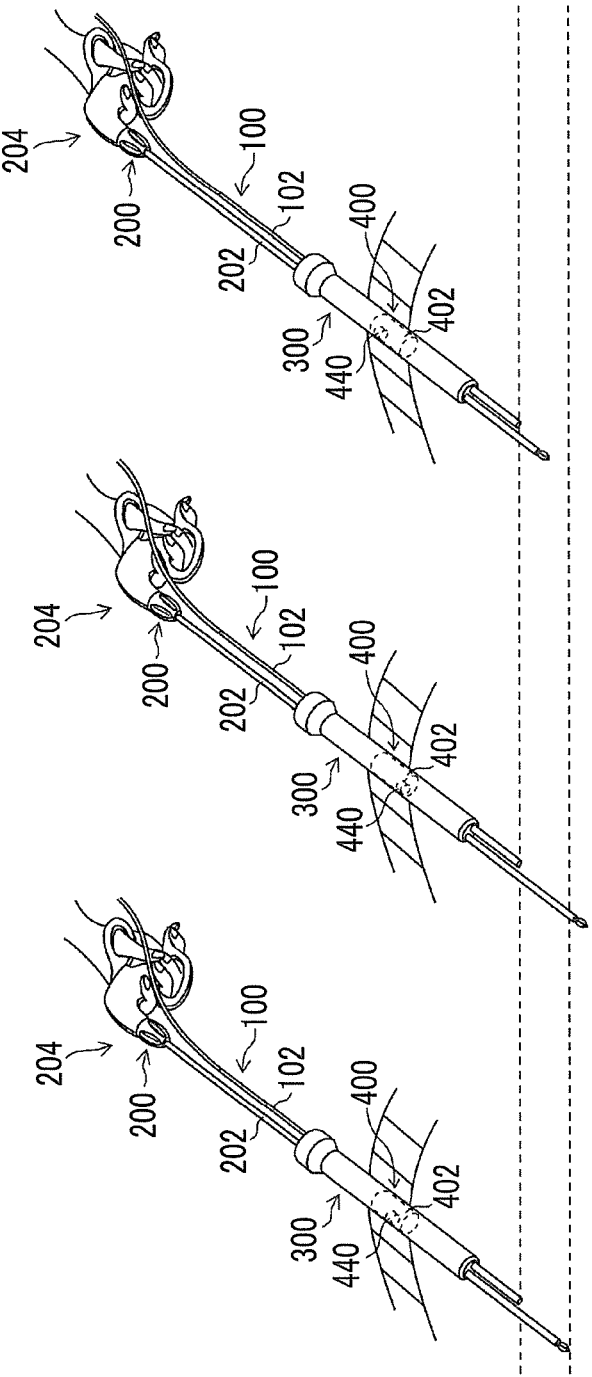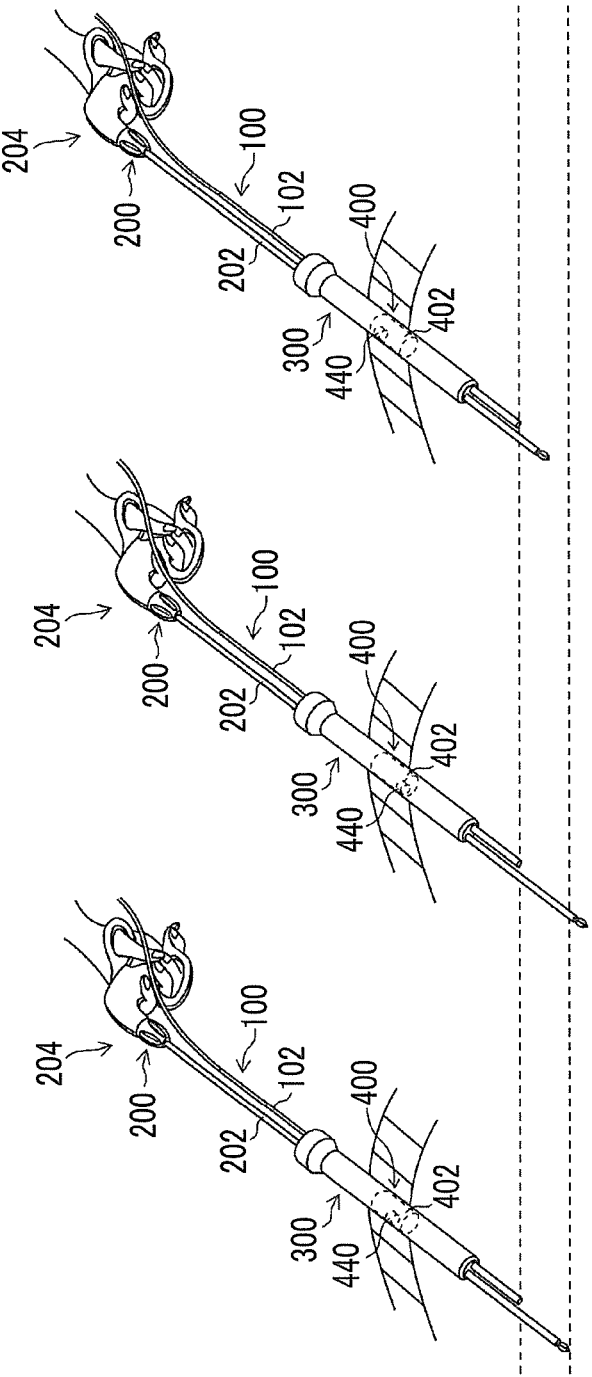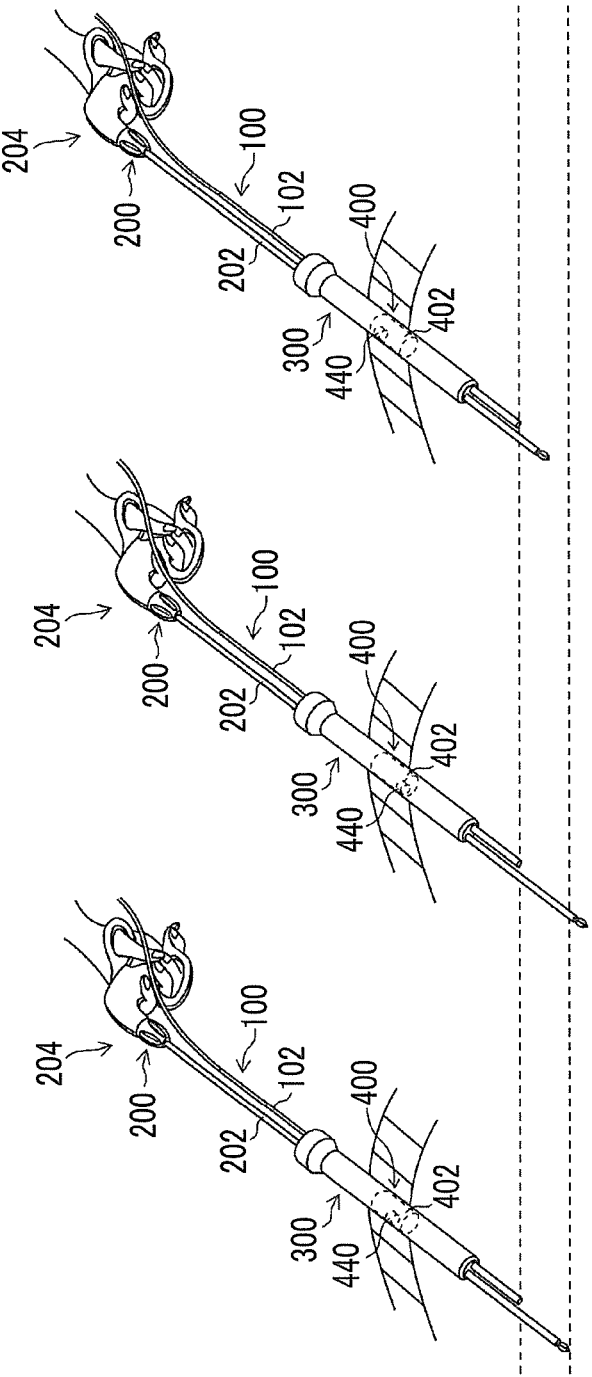

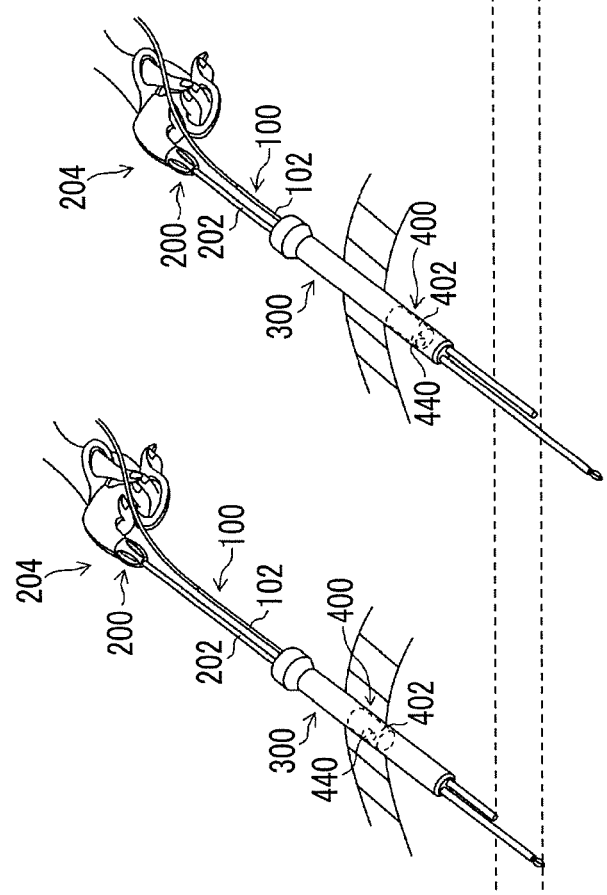

OVERTUBE AND ENDOSCOPIC SURGICAL DEVICE

CROSS-REFERENCE TO RELATED APPLICATIONS

This application is a Continuation of PCT International Application No. PCT/JP2015/059350 filed on Mar. 26, 2015, which claims priority under 35 U.S.C. § 119(a) to U.S. Provisional Application No. 61/971,102 filed on Mar. 27, 2014. Each of the above applications is hereby expressly incorporated by reference, in their entirety, into the present application.

BACKGROUND OF THE INVENTION

1. Field of the Invention

The present invention relates to an overtube and an endoscopic surgical device, and particularly, to an overtube and an endoscopic surgical device that has a function of cleaning an observation window of an endoscope.

2. Description of the Related Art

In recent years, since invasion to a patient is small compared to surgery in which a laparotomy, a thoracotomy, or the like, is performed, endoscopic surgery using endoscopes (hard endoscopes), such as a laparoscope, has been widely performed. In endoscopic surgery, a plurality of holes are made in a patient's body wall, an endoscope is inserted into a body cavity from one hole of these and a treatment tool is inserted into the body cavity from another hole. Then, treatment of a living body tissue is performed with the treatment tool while observing the living body tissue within the body cavity with the endoscope.

Generally, in endoscopic surgery, one or a plurality of treatment tools are used simultaneously with the endoscope. Therefore, since it is difficult for one surgeon to simultaneously operate the endoscope and the plurality of treatment tools, for example, a task, such as operating a treatment tool that the surgeon holds with his/her hands while making an assistant called an endoscopic technician operate the endoscope is normally performed.

Additionally, in endoscopic surgery, an overtube called a trocar, or the like is used. The overtube consists of a cylindrical body inserted into a body wall, and is a guide instrument for introducing instruments, such as the endoscope and a treatment tool, into the body cavity.

Meanwhile, a distal end of an insertion part of the endoscope is provided with an observation window, and observation within the body cavity is performed via the observation window. Therefore, although it is always necessary to keep the observation window clean, foreign matter (mucus, fats and oils, tissue pieces, or the like) may adhere to the distal end of the insertion part of the endoscope introduced into the body cavity via the overtube. In this case, since an image of a site to be treated and the treatment tool becomes unclear, operations such as a surgeon first extracting the insertion part of the endoscope from the overtube and then wiping the observation window are required. Therefore, surgery time may be lengthened or a surgeon may miss a site to be treated, which causes degradation in surgical efficiency.

Additionally, there are also many situations where foreign matter adheres to the inside of the overtube, and even if the observation window is cleaned after the insertion part of the endoscope is first extracted from the overtube, the foreign matter may adhere to the observation window when the insertion part of the endoscope is inserted again into the overtube.

As opposed to such a problem, for example, JP2010-17559A discloses that the cylindrical body (sheath) that covers the insertion part (observation instrument for surgery) of the endoscope has a function of cleaning the observation window (observation element). A fluid supply and discharge port through which cleaning water is allowed to be supplied to and suctioned from a distal end side (body cavity side) of an insertion passage through which the insertion part of the endoscope is inserted is provided inside this cylindrical body. A distal end surface of the insertion part of the endoscope is positioned in the vicinity of the fluid supply and discharge port, and when cleaning water is supplied to or suctioned from the fluid supply and discharge port, cleaning of the observation window is performed.

SUMMARY OF THE INVENTION

However, in the technique disclosed in JP2010-17559A, since both the observation within the body cavity and the cleaning of the observation window are performed in a state where the distal end of the insertion part of the endoscope is housed inside the cylindrical body, this becomes a factor by which the visual field of the observation window is hindered by the cleaning water that has remained within the insertion passage. Particularly, cleaning water may be apt to remain at a corner of a distal end depression (recess space) defined by a distal end side inner wall surface of the insertion passage of the cylindrical body, and the distal end surface of the insertion part of the endoscope, and it may be difficult to secure an excellent field of view.

The invention has been made in view of such circumstances, and an object thereof is to provide an overtube and an endoscopic surgical device that can remove foreign matter adhering to an observation window of an endoscope with a simple operation, and can always guarantee an excellent field of view.

In order to achieve the above object, an overtube related to an aspect of the invention includes a cylindrical body having a distal end, a base end, and a longitudinal axis; a distal end opening provided at the distal end of the cylindrical body; a base end opening provided at the base end of the cylindrical body; an endoscope insertion passage that is provided along the longitudinal axis of the cylindrical body, couples the distal end opening and the base end opening together, and allows an endoscope insertion part to be inserted therethrough so as to be movable forward and backward; a fluid passage having a fluid supply and discharge port opening to an inside of the endoscope insertion passage on a distal end side thereof, and a base-end-side connection port connected to a fluid supply and suction device that supplies and suctions a fluid; and a positioning mechanism that positions a distal end of the endoscope insertion part at a first position closer to a base end side than a distal-end-side end of the fluid supply and discharge port. The positioning mechanism includes locking means (locking part) for locking the endoscope insertion part to the cylindrical body when the endoscope insertion part moves to the base end side along the longitudinal axis of the cylindrical body.

According to this aspect, in a case where foreign matter adheres to the observation window of the endoscope insertion part introduced into the body cavity via the overtube, a state where cleaning of the observation window is allowed without extracting the endoscope insertion part from the overtube is brought about by positioning the distal end of the endoscope insertion part at a predetermined position inside the cylindrical body. Then, the foreign matter adhering to the observation window can be removed by supplying and suctioning a fluid from the fluid supply and discharge port. Thereafter, a state where the inside of a body cavity can be observed without being influenced by fluid remaining in the endoscope insertion passage can be brought about by delivering the distal end of the endoscope insertion part again from the distal end opening of the cylindrical body. Therefore, foreign matter adhering to the observation window of the endoscope insertion part, can be removed with a simple operation, and an excellent field of view can be always guaranteed.

In the overtube related to the aspect of the invention, an aspect in which the first position is a position where a plane including the distal end of the endoscope insertion part intersects the fluid supply and discharge port is preferable.

In the overtube related to the aspect of the invention, an aspect in which the fluid supply and discharge port is provided in a fluid passage having a longitudinal axis that intersects a plane including the distal end of the endoscope insertion part positioned at the first position by the positioning mechanism is preferable.

In the endoscopic surgical device related to the aspect of the invention, an aspect in which the fluid passage is provided independently from the endoscope insertion passage is preferable.

In the endoscopic surgical device related to the aspect of the invention, an aspect in which the locking means has a projection provided in the endoscope insertion passage, and the endoscope insertion part is locked to the cylindrical body by striking a step provided in the endoscope insertion part against the projection when the endoscope insertion part moves to the base end side along the longitudinal axis of the cylindrical body is preferable.

In the endoscopic surgical device related to the aspect of the invention, an aspect in which a sleeve member that is fitted to an outer periphery of the endoscope insertion part and moves forward and backward integrally with the endoscope insertion part is provided inside the endoscope insertion passage, and the locking means has a projection provided in the endoscope insertion passage, and the endoscope insertion part is locked to the cylindrical body by striking the sleeve member fitted to the outer periphery of the endoscope insertion part against the projection when the endoscope insertion part moves to the base end side along the longitudinal axis of the cylindrical body is preferable.

An endoscopic surgical device related to another aspect of the invention includes an endoscope including an endoscope insertion part having an observation window arranged at a distal end thereof; a cylindrical body having a distal end, a base end, and a longitudinal axis, the cylindrical body including a distal end opening provided at the distal end of the cylindrical body, a base end opening provided at the base end of the cylindrical body, an endoscope insertion passage that is provided along the longitudinal axis of the cylindrical body, couples the distal end opening and the base end opening together, and allows the endoscope insertion part to be inserted therethrough so as to be movable forward and backward, and a fluid passage having a fluid supply and discharge port opening to an inside of the endoscope insertion passage on a distal end side thereof; a fluid supply and suction device that is connected to a base end side of the fluid passage and supplies and suctions a fluid; and a positioning mechanism that positions a distal end of the endoscope insertion part at a first position closer to a base end side than a distal-end-side end of the fluid supply and discharge port when the endoscope insertion part moves to the base end side along the longitudinal axis of the cylindrical body.

In the endoscopic surgical device related to the other aspect of the invention, an aspect in which the first position is a position where a plane including the distal end of the endoscope insertion part intersects the fluid supply and discharge port is preferable.

In the endoscopic surgical device related to the other aspect of the invention, an aspect in which the fluid supply and discharge port is provided in a fluid passage having a longitudinal axis that intersects a plane including the distal end of the endoscope insertion part is preferable.

In the endoscopic surgical device related to the other aspect of the invention, an aspect in which the positioning mechanism is locking means for locking the endoscope insertion part to the cylindrical body when the endoscope insertion part moves to the base end side along the longitudinal axis of the cylindrical body is preferable.

In the endoscopic surgical device related to the other aspect of the invention, an aspect in which the locking means includes a step provided in the endoscope insertion part and a projection provided in the endoscope insertion passage of the cylindrical body, and at least one of the step and the projection is an elastic body is preferable.

An endoscopic surgical device according to still another aspect of the invention includes an endoscope including an endoscope insertion part having an observation window arranged at a distal end thereof; a cylindrical body having a distal end, a base end, and a longitudinal axis, the cylindrical body including a distal end opening provided at the distal end of the cylindrical body, a base end opening provided at the base end of the cylindrical body, an endoscope insertion passage that is provided along the longitudinal axis of the cylindrical body, couples the distal end opening and the base end opening together, and allows the endoscope insertion part to be inserted therethrough so as to be movable forward and backward, and a fluid passage having a fluid supply and discharge port opening to an inside of the endoscope insertion passage on a distal end side thereof; and a fluid supply and suction device that is connected to a base end side of the fluid passage and supplies and suctions a fluid. The endoscope insertion part is provided with a positioning part that positions a distal end of the endoscope insertion part at a first position closer to a base end side than a distal-end-side end of the fluid supply and discharge port when the endoscope insertion part moves to the base end side along the longitudinal axis of the cylindrical body. When a distance from the fluid supply and discharge port to the base end opening is L, the positioning part includes an indicator provided at a position separated by the distance L from the distal end of the endoscope insertion part toward the base end side.

According to the invention, foreign matter adhering to an observation window of an endoscope insertion part, can be removed with a simple operation, and an excellent field of view can be always guaranteed.

BRIEF DESCRIPTION OF THE DRAWINGS

FIG. 7 is an explanatory view used for the description of the action of the slider.

FIG. 8 is an explanatory view used for the description of the action of the slider.

FIG. 9 is an explanatory view used for the description of the action of the slider.

FIGS. 10A to 10C are explanatory view illustrating an aspect of the operation when treatment of a diseased site within a patient's body cavity is performed using the endoscopic surgical device.

FIGS. 11A to 11C are explanatory view illustrating an aspect of the operation when the treatment of the diseased site within the patient's body cavity is performed using the endoscopic surgical device.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
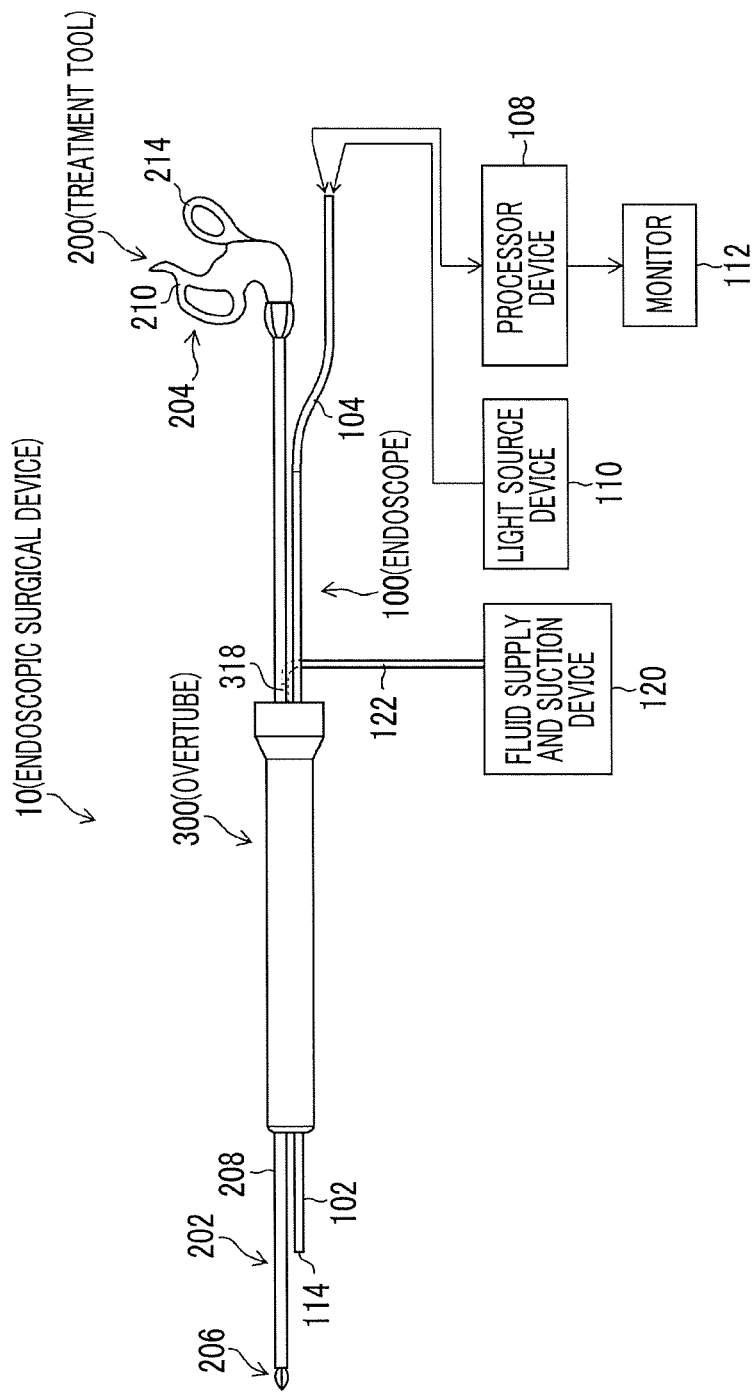
FIG. 1 is a schematic block diagram of an endoscopic surgical device related to the invention.

FIG. 1 is a schematic block diagram of an endoscopic surgical device related to the invention. As illustrated in FIG. 1, an endoscopic surgical device 10 includes an endoscope 100 that observes the inside of a patient's body cavity, a treatment tool 200 for examining or treating a diseased site within the patient's body cavity, and an overtube 300 that is inserted into a body wall and guides the endoscope 100 and the treatment tool 200 into the body cavity.

The endoscope 100 is, for example, a hard endoscope, such as a laparoscope, and includes an insertion part 102 (hereinafter referred to as "endoscope insertion part") that is inserted into a body cavity and has an outer peripheral part surrounded by an elongated hard tubular member, and a cable part 104 that is provided continuously with a base end side of the endoscope insertion part 102 and that has an outer peripheral part surrounded by an elongated flexible tubular member.

The cable part 104 indicates a flexible cable portion in which a wire rod, such as a cable or a light guide, which extends from a base end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 and a light source device 110 is detachably connected to the cable part via the connector. Additionally, the processor device 108 is connected to a monitor 112 via a cable.

Figure 2:
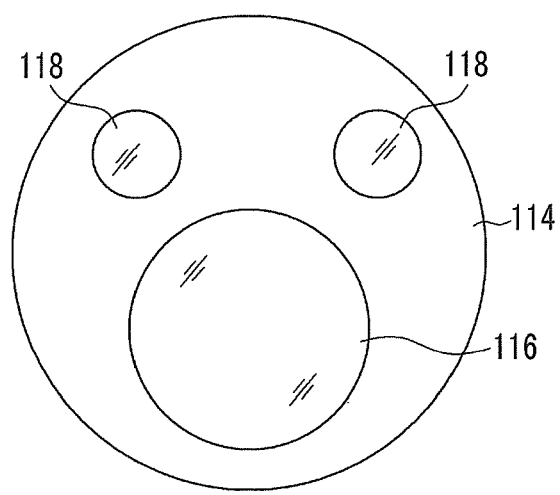
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

The observation window 116 is a constituent element of an observation part of the endoscope 100, and an objective lens of an observation optical system, and an image pick-up element, such as a charge coupled device (CCD) or a complementary metal oxide semiconductor (CMOS), which is arranged at an image pick-up position of the objective lens, are disposed behind the observation window 116. In addition, in the present specification, the observation window 116 is also a kind of lens, and cleaning of the observation window 116 is also referred to as lens cleaning as will be described below. A signal cable (not illustrated) connected to an image pick-up element of this observation part is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pick-up element, and is converted into electrical signals (image pick-up signals), and the electrical signals are output to the processor device 108 via the signal cable and are converted into video signals. Then, the video signals are output to the monitor 112 connected to the processor device 108, and the observation image (endoscope image) is displayed on a screen of the monitor 112.

An exit end of the light guide (not illustrated) is disposed behind the illumination windows 118 and 118 of FIG. 2. The light guide is inserted through the endoscope insertion part 102 and the cable part 104 of FIG. 1 and has an incident end disposed within the connector (not illustrated). Therefore, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more.

As illustrated in FIG. 1, the treatment tool 200 consists of, for example, forceps, and includes an elongated insertion part 202 (hereinafter referred to as a "treatment tool insertion part") that is inserted into a body cavity, an operating part 204 that is provided on the base end side of the treatment tool insertion part 202 and is gripped by a surgeon, and a treatment part 206 that is provided on a distal end side of the treatment tool insertion part 202 and is operable by the operation of the operating part 204.

The treatment tool insertion part 202 is provided with a cylindrical sheath 208, and an operating shaft (not illustrated) that is inserted into the sheath 208 so as to be movable in the direction of an axial center. Moreover, the operating part 204 is provided with a fixed handle 210, and a movable handle 214 that is turnably coupled to the fixed handle 210 via a turning pin. A base end of the operating shaft is coupled to the movable handle 214.

The treatment part 206 is provided with a pair of gripping members that is openable and closable. The gripping members are coupled to a distal end of the operating shaft via a driving mechanism (not illustrated). With the turning operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, an ultrasonic device, and an aspirator.

As illustrated in FIG. 1, the overtube 300 allows the endoscope insertion part 102 and the treatment tool insertion part 202, which are inserted thereinto from the base end side, to be inserted therethrough and delivered from the distal end side. By inserting the overtube 300 into a body wall and having a distal end side thereof arranged outside of the body and a base end side thereof arranged within the body cavity, it is possible to guide the endoscope insertion part 102 and the treatment tool insertion part 202 into the body cavity with one overtube 300. Additionally, the overtube 300 includes an interlocking function of interlocking the endoscope insertion part 102 with the treatment tool insertion part 202 to move these insertion parts forward and backward as will be described below in detail. For example, the endoscope insertion part 102 can also be moved forward and backward by the forward and backward movement operation of only the treatment tool insertion part 202, and a suitable observation image can be obtained without performing the forward and backward movement operation of the endoscope insertion part 102.

Figure 3:
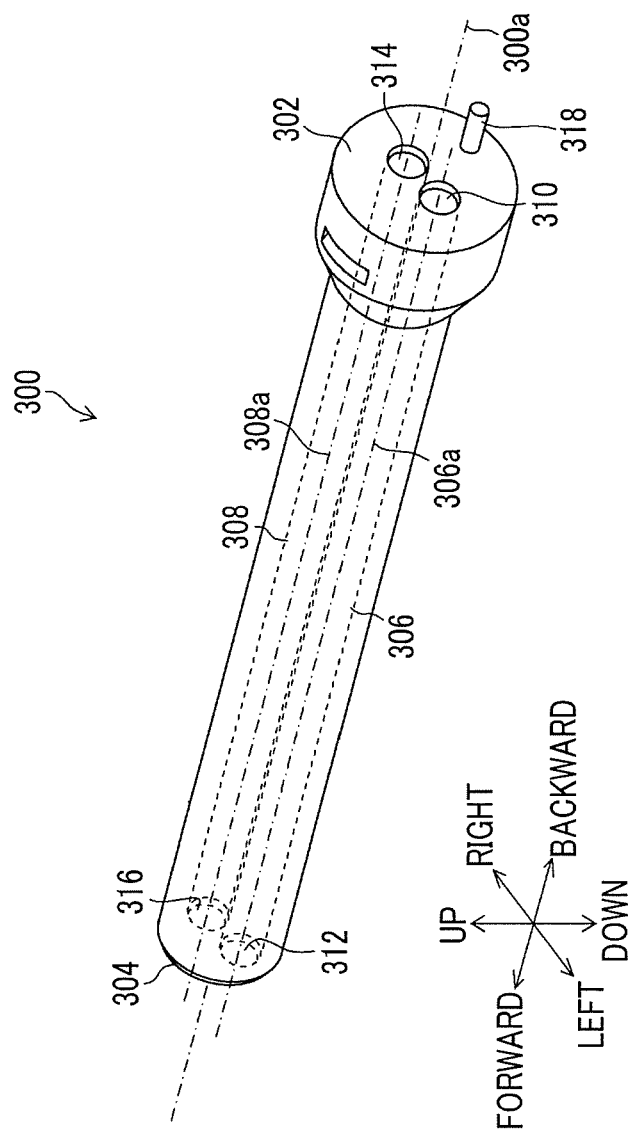
FIG. 3 is an external perspective view illustrating an overtube.

FIG. 3 is an external perspective view illustrating the overtube 300.

As illustrated in this drawing, the overtube 300 has an elongated columnar shape as a whole, and has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward. These insertion passages are parallel to a reference axis 300a (longitudinal axis) indicating a central axis of the overtube.

If a central axis of the endoscope insertion passage 306 is referred to as an endoscope insertion axis 306a and a central axis of the treatment tool insertion passage 308 is referred to as a treatment tool insertion axis 308a, the endoscope insertion axis 306a and the treatment tool insertion axis 308a are parallel to each other, and is also parallel to the reference axis 300a. The endoscope insertion axes 306a and the treatment tool insertion axes 308a are equivalent to positions of the central axes of the endoscope insertion part 102 and the treatment tool insertion part 202 that are respectively inserted through the endoscope insertion passage 306 and the treatment tool insertion passage 308. Additionally, in the present embodiment, the reference axis 300a, the endoscope insertion axis 306a, and the treatment tool insertion axis 308a are arranged on the same plane. However, a configuration in which the reference axis 300a, the endoscope insertion axis 306a, and the treatment tool insertion axis 308a are arranged on the same plane may not be adopted.

In addition, regarding the position and orientation of a space where the overtube 300 has been arranged, terms called forward, backward, left, right, up, and down are used with the orientation from the base end surface 302 in a direction along the reference axis 300a to the distal end surface 304 defined as the forward and with the orientation from the reference axis 300a to the endoscope insertion axis 306a defined as the left.

The base end surface 302 of the overtube 300 is provided with an endoscope insertion port 310 that is a base end opening that allows the endoscope insertion part 102 to be inserted into the endoscope insertion passage 306 therethrough, and a treatment tool insertion port 314 that is base end opening that allows the treatment tool insertion part 202 to be inserted into the treatment tool insertion passage 308 therethrough.

The distal end surface 304 of the overtube 300 is provided with an endoscope delivery port 312 that is a distal end opening that allows the endoscope insertion part 102 inserted into the endoscope insertion passage 306 to be delivered to the outside therethrough, and a treatment tool delivery port 316 that is a distal end opening that allows the treatment tool insertion part 202 inserted into the treatment tool insertion passage 308 to be delivered to the outside therethrough.

Additionally, the base end surface 302 of an overtube 300 is provided with a cleaning connector 318. One end of a water supply tube 122 illustrated in FIG. 1 is connected to the cleaning connector 318 (base-end-side connection port), and the other end thereof is connected to the fluid supply and suction device 120 (fluid supply and suction means). Although it will be described in detail, the fluid supply and suction device 120 is a device used for the below-mentioned lens cleaning function which cleans the observation window 116 provided in the distal end surface 114 of the endoscope insertion part 102, and has a function to perforin supply and suction of cleaning water (arbitrary cleaning liquids).

If cleaning water is supplied from the fluid supply and suction device 120 to a pipe line of the water supply tube 122, the cleaning water is sent from the cleaning connector 318 to a fluid passage formed inside the overtube 300, and is delivered from a fluid supply and discharge port 500 (to be described b below) that opens to the inside of the endoscope insertion passage 306 on the distal end side through the fluid passage. Additionally, if the pipe line of the water supply tube 122 is suctioned by the fluid supply and suction device 120, the fluid passage within the water supply tube 122 and the overtube 300 is decompressed, and suction of the fluid (supplied cleaning water or the like) from the fluid supply and discharge port 500 is performed.

Figure 4:
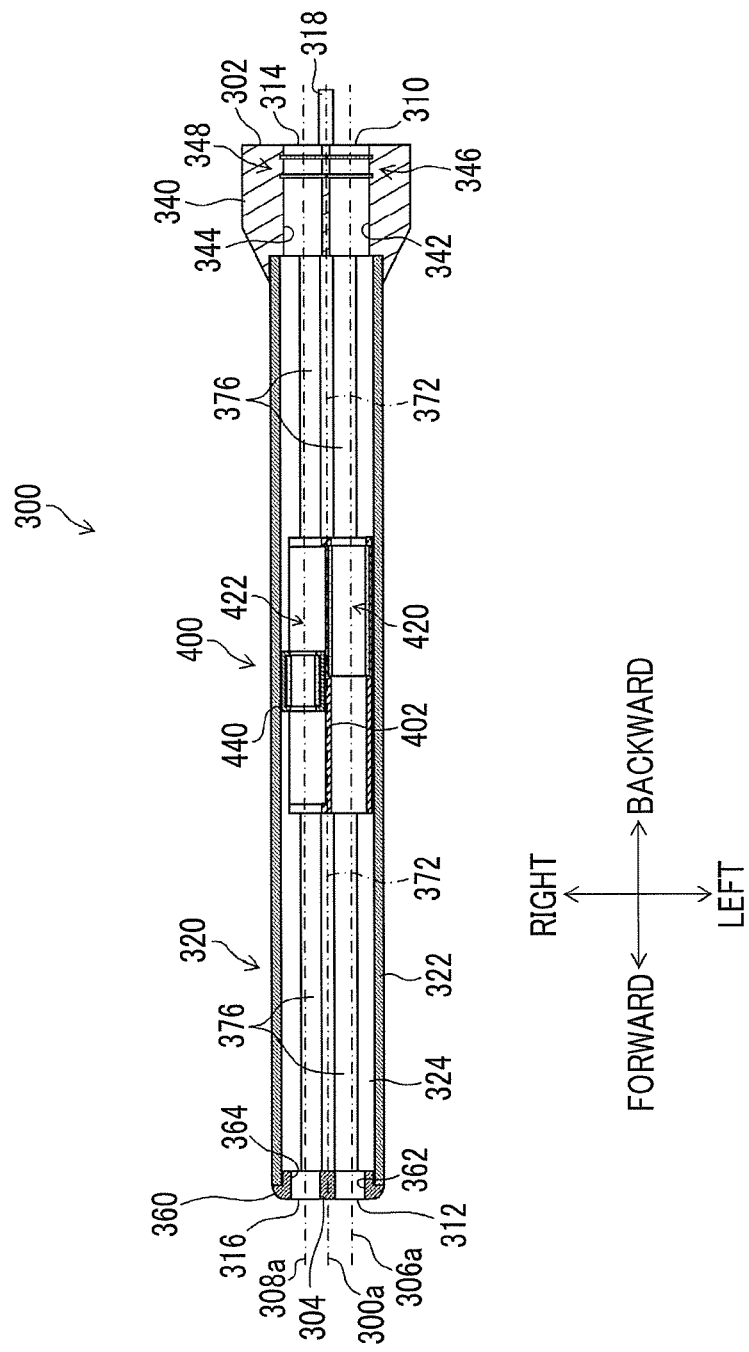
FIG. 4 is a sectional view illustrating the internal structure of the overtube.

FIG. 4 is a sectional view illustrating the internal structure of the overtube 300, and illustrates a section cut in a plane that includes the reference axis 300a and is orthogonal to an upward-downward direction (cut in a leftward-rightward direction along the reference axis 300a).

As illustrated in this drawing, the overtube 300 has an overtube body 320 that is a cylindrical body that occupies substantially the entire area in the forward-backward direction, a base end cap 340 that is attached to a rear end (base end) of the overtube 300, a distal end cap 360 that is attached to a distal end, and a slider 400 (an interlinking member) that is arranged inside the overtube 300.

The overtube body 320 is formed in an elongated cylindrical shape having the reference axis 300a as a central axis using hard resins, metals, or the like, and has an outer wall 322 that surrounds an outer periphery, and a cavity part 324 that penetrates from a base end of the overtube body 320 to a distal end thereof.

The cavity part 324 includes spaces serving as the endoscope insertion passage 306 and the treatment tool insertion passage 308, and houses the slider 400 and the like.

The base end cap 340 is formed in a columnar shape of which the diameter is made larger than the external diameter of the overtube body 320 using hard resins, metals, or the like, and a rear end surface thereof constitutes the base end surface 302 of the overtube 300. The base end cap 340 is provided with a through-hole 342 and a through-hole 344 that form a portion of the endoscope insertion passage 306 and a portion of the treatment tool insertion passage 308, respectively. In the base end surface 302, an opening of the through-hole 342 is equivalent to the above-described endoscope insertion port 310, and an opening of the through-hole 344 is equivalent to the above-described treatment tool insertion port 314.

Additionally, the through-holes 342 and 344 are provided with valve members 346 and 348. The valve members 346 and 348, for example, open in a case where the endoscope insertion part 102 and the treatment tool insertion part 202 are inserted therethrough and come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

Moreover, a through-hole (not illustrated) that communicates with the pipe line of the elongated cylindrical cleaning connector 318 illustrated in FIG. 1 and penetrates from the base end surface 302 to the cavity part 324 of the overtube body 320 is formed in the base end cap 340, and the through-hole is used as a portion of the fluid passage provided in the overtube 300 for a lens cleaning function to be described below. The detailed description will be made below.

The distal end cap 360 is formed of hard resins, metals, or the like, and a front end surface thereof constitutes the distal end surface 304 of the overtube 300. The distal end cap 360 is provided with a through-hole 362 and a through-hole 364 that form a portion of the endoscope insertion passage 306 and a portion of the treatment tool insertion passage 308, respectively. In the distal end surface 304, an opening of the through-hole 362 is equivalent to the above-described endoscope delivery port 312, and an opening of the through-hole 364 is equivalent to the treatment tool delivery port 316.

Additionally, in the distal end cap 360, a fluid supply and discharge port 500 (not illustrated in FIG. 4) for the lens cleaning function to be described below is formed in an inner wall surface of the through-hole 362, and a through-hole that penetrates from the cavity part 324 of the overtube body 320 to the fluid supply and discharge port 500 is formed as a portion of the fluid passage provided in the overtube 300 for the lens cleaning function.

The above base end cap 340 and the above distal end cap 360 are some of the constituent elements of the overtube body of the invention, and may be formed separately from or formed integrally with the overtube body 320.

The slider 400 is housed within (the cavity part 324) the overtube body 320, and is supported so as to be movable forward and backward in the direction of the reference axis 300a. The slider 400 is an interlocking member that is coupled to the endoscope insertion part 102 inserted through the endoscope insertion passage 306 and the treatment tool insertion part 202 inserted through the treatment tool insertion passage 308 and that has a dead zone where the forward and backward movement of any of the endoscope insertion part 102 and the treatment tool insertion part 202 in the forward-backward direction (axial direction) does not interlock with the movement of the other and a sensing zone where the forward and backward movement of any of the endoscope insertion part 102 and the treatment tool insertion part 202 interlocks with the movement of the other. That is, the endoscope insertion part 102 is adapted to interlock with the forward and backward movement of the treatment tool insertion part 202 in the axial direction with play by the slider 400.

Figure 5:
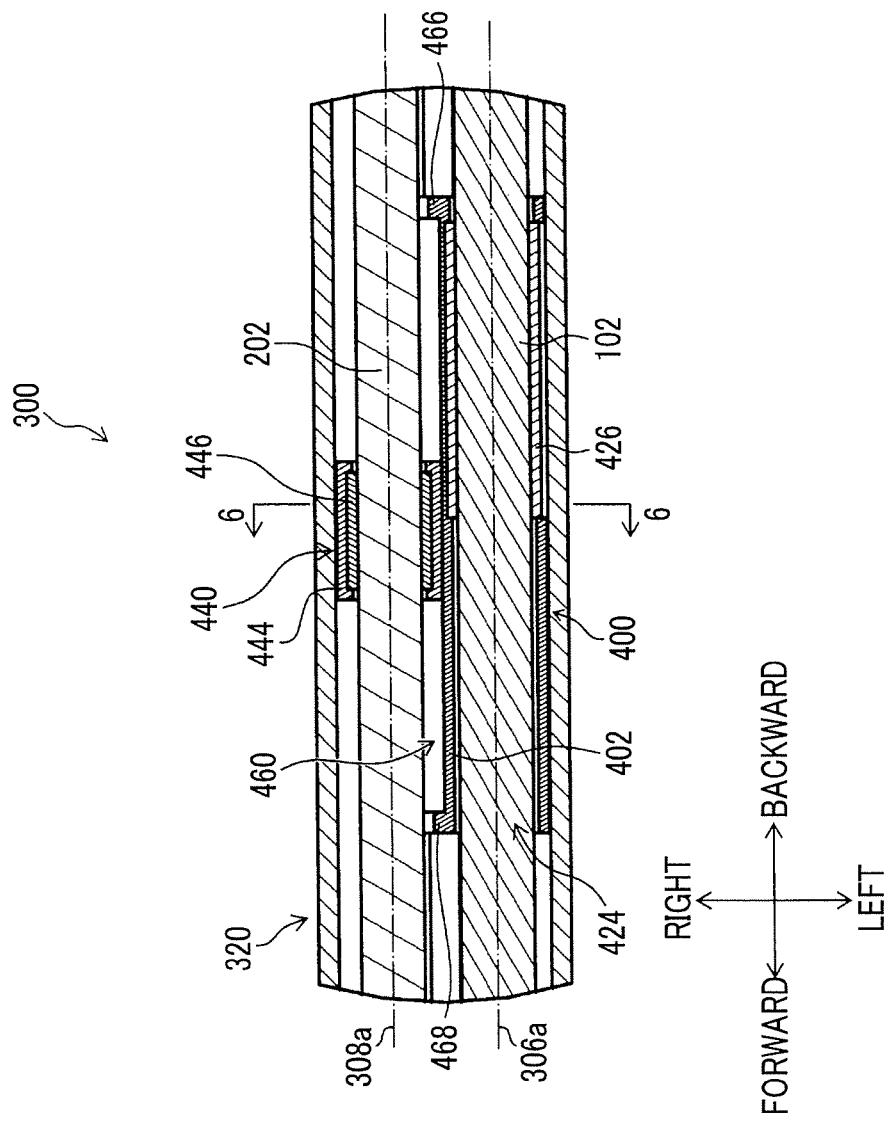
FIG. 5 is an enlarged sectional view illustrating a portion of FIG. 4 in an enlarged manner.
Figure 6:
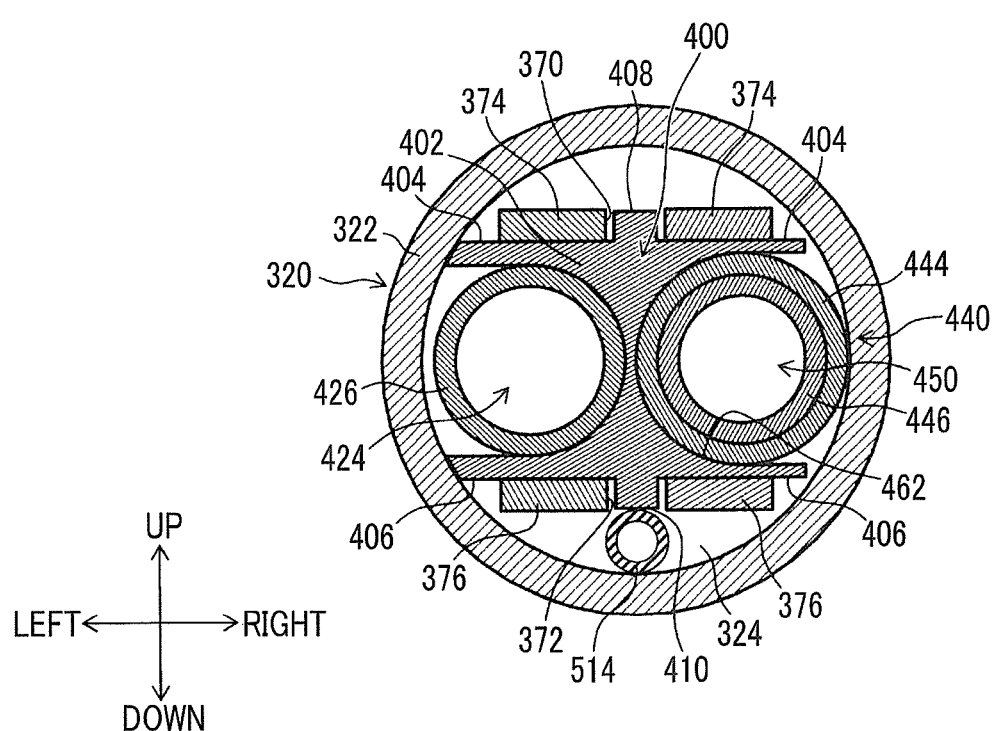
FIG. 6 is a sectional view when viewed from arrow 6-6 in FIG. 5.

FIG. 5 is an enlarged sectional view illustrating a portion, in which the slider 400 is arranged in FIG. 4, in an enlarged manner, and illustrates a state where the endoscope insertion part 102 and the treatment tool insertion part 202 have been inserted through the endoscope insertion passage 306 and the treatment tool insertion passage 308, respectively. FIG. 6 is a sectional view when viewed from arrow 6-6 in FIG. 5.

As illustrated in FIGS. 5 and 6, the slider 400 has a slider body 402 (slider member) that holds components of the slider 400. As illustrated in FIG. 6, protruding strips 408 and 410 that extend in the direction (forward-backward direction) of the reference axis 300a are formed on a flat upper surface 404 and a flat lower surface 406 of the slider body 402.

Meanwhile, a pair of left and right long plate-shaped guide plates 374 and 374 and a pair of left and right long plate-shaped guide plates 376 and 376, which are laid between the base end cap 340 and the distal end cap 360, are respectively supported by an upper part and a lower part within the overtube body 320, and guide grooves 370 and 372, which extend in the direction of the reference axis 300a from the base end cap 340 to the distal end cap 360, are formed by a gap between the guide plates 374 and 374 and a gap between the guide plates 376 and 376.

The protruding strips 408 and 410 of the slider body 402 are respectively fitted into the guide grooves 370 and 372 within the overtube body 320, and the upper surface 404 and the lower surface 406 are arranged in a state where these surfaces have contacted or approached the guide plates 374 and 374 and the guide plates 376 and 376.

Accordingly, the slider 400 is supported so as to be movable forward and backward in the forward-backward direction within the overtube body 320, and is supported in a state where the movement of the slider in the upward-downward direction and in the leftward-rightward direction and the rotation of the slider in all directions (direction around three axes including a forward-backward axis, a leftward-rightward axis, and an upward-downward direction) are restricted (a state where the rotation of the slider around at least the reference axis 300a is impossible). Additionally, the slider 400 moves forward and backward within a movable range having a position where the slider abuts against the base end cap 340 as a rear end, and having a position where the slider abuts against the distal end cap 360 as a front end.

In addition, the guide grooves 370 and 372 may not be formed by the guide plates 374 and 374 and the guide plates 376 and 376 arranged within the overtube body 320, and may be formed in the outer wall 322 of the overtube body 320 or may be formed by other configurations.

Additionally, the slider 400, as illustrated in FIG. 4, has an endoscope-coupled part 420 that is coupled to (engaged with) the endoscope insertion part 102, and a treatment tool-coupled part 422 that is coupled to (engaged with) the treatment tool insertion part 202.

The endoscope-coupled part 420 is provided on the left side of the slider body 402, and includes a through-hole 424 (refer to FIG. 6) in which a space serving as the endoscope insertion passage 306 is secured within the overtube body 320 and through which, as illustrated in FIG. 5, the endoscope insertion part 102 is inserted, and a pressure-contact member 426 that is fixed to the through-hole 424, is brought into pressure contact with the outer peripheral surface (side surface) of the endoscope insertion part 102 inserted through the endoscope insertion passage 306. The pressure-contact member 426 is annularly formed of elastic materials, such as elastic rubber, as illustrated in FIG. 6.

Accordingly, when the endoscope insertion part 102 has been inserted through the endoscope insertion passage 306, as illustrated in FIG. 5, the endoscope insertion part 102 is inserted through the through-hole 424, the pressure-contact member 426 is brought into pressure contact with (engaged with) the outer peripheral surface of the endoscope insertion part 102, and the central axis of the endoscope insertion part 102 is arranged coaxially with the endoscope insertion axis 306a.

The endoscope insertion part 102 and the slider 400 (slider body 402) are coupled to (engaged with) each other in an interlockable manner via the pressure-contact member 426, and the slider 400 (slider body 402) also integrally moves forward and backward in an interlocking manner with the forward and backward movement of the endoscope insertion part 102 in the forward-backward direction (axial direction).

In addition, since the coupling herein is based on the elastic force of the pressure-contact member 426, the engagement position (the position of the endoscope insertion part 102 where the slider 400 is engaged) of the endoscope insertion part 102 coupled to the slider 400 (slider body 402) can be arbitrarily adjusted.

The treatment tool-coupled part 422, as illustrated in FIG. 4, is provided on the right side of the slider body 402, and as illustrated in FIG. 5, includes a sleeve 440 (sleeve member) that is coupled to the treatment tool insertion part 202, and a guide part 460 that guides the sleeve 440 so as to be movable forward and backward in the forward-backward direction.

The sleeve 440, as illustrated in FIG. 6, includes a sleeve body (frame body) 444 formed in a cylindrical shape, and a pressure-contact member 446 fixed to the inside of the sleeve body 444. The pressure-contact member 446 is annularly formed of elastic materials, such as elastic rubber.

Accordingly, when the treatment tool insertion part 202 has been inserted through the treatment tool insertion passage 308, as illustrated in FIG. 5, the treatment tool insertion part 202 is inserted through the inside (the through-hole 450 of FIG. 6) of the pressure-contact member 446, the pressure-contact member 446 is brought into pressure contact with (engaged with) the outer peripheral surface of the treatment tool insertion part 202, and the central axis of the treatment tool insertion part 202 is arranged coaxially with the treatment tool insertion axis 308a.

The treatment tool insertion part 202 and the sleeve 440 are coupled with each other in an interlockable manner via the pressure-contact member 446, and the sleeve 440 also integrally moves forward and backward in an interlocking manner with the forward and backward movement of the treatment tool insertion part 202 in the forward-backward direction (axial direction).

Additionally, the sleeve 440 also rotates with respect to the slider body 402 in an interlocking manner with the rotation of the treatment tool insertion part 202 around the axis thereof.

In addition, since the coupling between the treatment tool insertion part 202 and the sleeve 440 herein is based on the elastic force of the pressure-contact member 446, the engagement position (the position of the treatment tool insertion part 202 where the sleeve 440 is engaged) of the treatment tool insertion part 202 coupled to the sleeve 440 can be arbitrarily adjusted.

Meanwhile, the guide part 460 of the treatment tool-coupled part 422, as illustrated in FIG. 6, is formed by a space surrounded by a guide surface 462 of the slider body 402 that extends in the direction of the reference axis 300a within the cavity part 324 of the overtube body 320, and an inner peripheral surface of the overtube body 320. The sleeve 440 is housed and arranged in the space of the guide part 460, is supported so as to be movable in the forward-backward direction and rotatable around its axis, and is supported in a state where the movement of the sleeve in the upward-downward direction and in the leftward-rightward direction is restricted.

Additionally, the guide part 460 is provided so as to fall within a range from a base end of the slider body 402 to a distal end thereof, and as illustrated in FIG. 5, has end edge parts 466 and 468, which are formed to protrude in a direction orthogonal to the guide surface 462 along an end edge of the guide surface 462, respectively, on the base end side and the distal end side of the slider body 402.

The end edge parts 466 and 468 abut against the end of the sleeve 440 to restrict the movement of the sleeve 440, when the sleeve 440 arranged in the space of the guide part 460 moves forward and backward in the forward-backward direction.

Therefore, the sleeve 440 moves forward and backward within a movable range having a position where the sleeve abuts against the end edge part 466 as a rear end, and having a position where the sleeve abuts against the end edge part 468 as a front end. However, the rear end and the front end of the movable range of the sleeve 440 may not be restricted by the end edge part 466 and the end edge part 468.

According to the slider 400 configured as described above, the endoscope insertion part 102 inserted through the endoscope insertion passage 306 of the overtube 300 and the slider body 402 are coupled together, and the treatment tool insertion part 202 inserted through the treatment tool insertion passage 308 of the overtube 300 and the sleeve 440 are coupled together.

As illustrated in FIG. 7, it is supposed that a surgeon performs a forward and backward movement operation for moving the treatment tool insertion part 202 forward and backward in the axial direction (forward-backward direction) in a state where the sleeve 440 has not reached the rear end and the front end of the movable range thereof with respect to the slider body 402 (guide part 460).

In this case, in a case where the sleeve 440 has moved forward and backward within the movable range thereof with respect to the slider body 402, the slider body 402 does not move with respect to the forward and backward movement of the treatment tool insertion part 202. Therefore, a forward and backward movement operation in the dead zone where the endoscope insertion part 102 does not interlock with the forward and backward movement of the treatment tool insertion part 202 is performed.

Meanwhile, as illustrated in FIG. 8, if the treatment tool insertion part 202 is operated to move forward in a state where the sleeve 440 reaches the front end of the movable range thereof with respect to the slider body 402, the sleeve 440 and the slider body 402 move forward with respect to the overtube body 320 together with the treatment tool insertion part 202. Accordingly, a forward and backward movement operation in the sensing zone where the endoscope insertion part 102 moves forward in an interlocking manner with the treatment tool insertion part 202 is performed.

Similarly, as illustrated in FIG. 9, if the treatment tool insertion part 202 is operated to move backward in a state where the sleeve 440 reaches the rear end of the movable range thereof with respect to the slider body 402, the sleeve 440 and the slider body 402 move backward with respect to the overtube body 320 together with the treatment tool insertion part 202. Accordingly, a forward and backward movement operation in the sensing zone where the endoscope insertion part 102 moves backward in an interlocking manner with the treatment tool insertion part 202 is performed.

Therefore, in a case where the treatment tool insertion part 202 has been greatly displaced in the axial direction as described above (in a case where a large amplitude of forward and backward movement has been performed), the endoscope insertion part 102 is displaced in the axial direction in an interlocking manner with the treatment tool insertion part 202, and in a case where the displacement of the treatment tool insertion part 202 in the axial direction is small (in a case where a small amplitude of forward and backward movement is performed), the endoscope insertion part 102 is not displaced in the axial direction.

Accordingly, in a case where the displacement of the treatment tool insertion part 202 in the axial direction is large (in a case where a large amplitude of forward and backward movement has been performed) when a surgeon has moved the treatment tool insertion part 202 forward and backward in the axial direction, the endoscope insertion part 102 also moves in an interlocking manner forward, backward, up, down, right, and left. Thus, the visual field, orientation, and the like of the endoscope 100 can be changed as intended by a surgeon. Additionally, the visual field is always given to pick up an image of a treatment tool distal end, and consequently, an image that is optimal for treatment is automatically provided. In a case where it is desired to check sites other than a site to be treated, the checking can be performed by moving the treatment tool insertion part 202, and a surgeon can perform operations as desired. Therefore, an assistant (endoscopic technician) who operates the endoscope 100 apart from the surgeon can be made unnecessary, and a troublesome condition in which the surgeon should instruct an assistant about the visual field, orientation, and the like of the endoscope serially can be eliminated.

Additionally, in a case where the displacement of the treatment tool insertion part 202 in the axial direction is small (in a case where a small amplitude of forward and backward movement has been performed), the endoscope insertion part 102 does not interlock. Therefore, the size of an object to be observed within an observation image can be prevented from fluctuating unnecessarily, a sense of perspective can be suitably maintained, and a stable observation image can be provided.

FIGS. 10A to 11C are explanatory views illustrating aspects of the operation when treatment of a diseased site within a patient's body cavity is performed using the endoscopic surgical device 10 of the present embodiment, FIGS. 10A to 10C illustrate an aspect of the operation (the forward and backward movement operation in the dead zone) when only the treatment tool 200 moves forward and backward, and FIGS. 11A to 11C illustrate an aspect of the operation (forward and backward movement operation in the sensing zone) when the treatment tool 200 moves forward and backward in an interlocking manner with the endoscope 100.

As illustrated in FIG. 10A, the endoscope 100 (endoscope insertion part 102) and the treatment tool 200 (treatment tool insertion part 202) are respectively inserted into the endoscope insertion passage 306 and the treatment tool insertion passage 308 of the overtube 300 after the overtube 300 is inserted into a patient's body wall and a pneumoperitoneum gas is injected into a body cavity. In this case, the endoscope 100 is coupled to the slider body 402 of the slider 400, and the treatment tool 200 is coupled to the sleeve 440 of the slider 400. Thus, when the sleeve 440 moves within a movable range thereof with respect to the slider body 402, the interlocking is performed with the dead zone (play) where the endoscope 100 does not interlock with the forward and backward movement of the treatment tool 200.

In this state, if the surgeon grips the operating part 204 of the treatment tool 200 and minutely moves the treatment tool 200 forward, only the treatment tool 200 moves forward in a state where the endoscope 100 is stationary as illustrated in FIG. 10B, with respect to the forward movement in the dead zone until the sleeve 440 of the slider 400 abuts against the front end of the movable range thereof.

Similarly, if the surgeon grips the operating part 204 of the treatment tool 200 and minutely moves the treatment tool 200 backward, only the treatment tool 200 moves backward in a state where the endoscope 100 is stationary as illustrated in FIG. 10C, with respect to the backward movement in the dead zone until the sleeve 440 of the slider 400 abuts against the rear end of the movable range thereof.

Therefore, since the endoscope 100 does not move forward and backward with respect to the minute forward and backward movement operation of the treatment tool 200, that is, the forward and backward movement operation thereof in the dead zone, the range of an observation image displayed on the monitor 112 does not change, the size of an object to be observed can be prevented from fluctuating in response to the minute displacement of the treatment tool 200, a sense of perspective can be suitably maintained, and a stable observation image can be obtained.

FIG. 11A illustrates that the overtube 300, the endoscope 100, and the treatment tool 200 are in the same state as those of FIG. 10A.

In this state, if the surgeon grips the operating part 204 of the treatment tool 200 and greatly moves the treatment tool 200 forward, the endoscope 100 moves forward in an interlocking manner with the forward movement of the treatment tool 200 through an interlocking function of the slider 400 as illustrated in FIG. 11B, after the forward movement in the dead zone until the sleeve 440 of the slider 400 abuts against the front end of the movable range.

Similarly, if the surgeon grips the operating part 204 of the treatment tool 200 and greatly moves the treatment tool 200 backward, the endoscope 100 moves backward in an interlocking manner with the backward movement of the treatment tool 200 through the interlocking function of the slider 400 as illustrated in FIG. 11C, after the backward movement in the dead zone until the sleeve 440 of the slider 400 abuts against the rear end of the movable range.

Therefore, since the endoscope 100 moves forward and backward with respect to a large forward and backward movement operation of the treatment tool 200, that is, the forward and backward movement operation thereof in the sensing zone, the range of an observation image displayed on the monitor 112 is continuously changed so as to follow the forward and backward movement of the treatment tool 200. Accordingly, since the size of an object to be observed changes in response to the operation of the treatment tool 200, an image desired by a surgeon can be simply obtained.

Next, the lens cleaning function of the above endoscopic surgical device 10 will be described below.

When the endoscope insertion part 102 is inserted through the endoscope insertion passage 306 of the overtube 300 inserted into a body wall and a distal end of the endoscope insertion part 102 is arranged within a body cavity, foreign matter (mucus, blood, oils and fats, tissue pieces, and the like) may adhere to the surface of the observation window 116 in the distal end surface 114 of the endoscope insertion part 102. In this case, since a treatment object in an observation image of the endoscope 100 and an image of the treatment tool 200 become faint, in a related-art device, it is necessary to first extract the endoscope insertion part 102 from the endoscope insertion passage 306 of the overtube 300 and then wipe off the foreign matter of the observation window 116. This causes delay of surgery time and missing a site to be treated, and causes degradation in surgical efficiency.

Meanwhile, the endoscopic surgical device 10 of the present embodiment has a lens cleaning function to clean the observation window 116 to remove the foreign matter adhering to the observation window 116, without extracting the endoscope insertion part 102 from the endoscope insertion passage 306 of the overtube 300.

Figure 12:
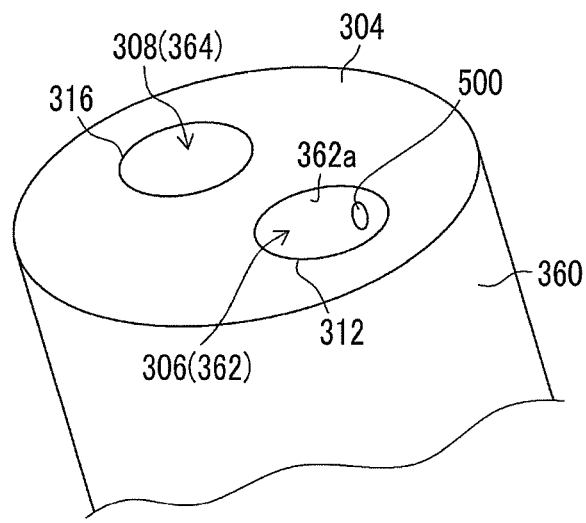
FIG. 12 is an enlarged perspective view illustrating a distal end surface of the overtube.

FIG. 12 is an enlarged perspective view illustrating the distal end cap 360 (distal end surface 304) that becomes a distal end of the overtube 300.

In this drawing, as described above, the distal end cap 360 of the distal end of the overtube 300 is provided with the through-hole 362 that forms a portion of the endoscope insertion passage 306, and the through-hole 364 that forms a portion of the treatment tool insertion passage 308, an opening of the through-hole 362 in the distal end surface 304 is equivalent to the endoscope delivery port 312 that allows the endoscope insertion part 102 inserted through the endoscope insertion passage 306 to be delivered therethrough, and an opening of the through-hole 364 in the distal end surface 304 is equivalent to the treatment tool delivery port 316 that allows the treatment tool insertion part 202 inserted through the treatment tool insertion passage 308 to be delivered therethrough.

An inner wall surface 362a (an inner wall surface 362a of the endoscope insertion passage 306) of the through-hole 362 that forms the endoscope insertion passage 306 out of the through-hole 362 and the through-hole 364 is provided with the fluid supply and discharge port 500 that allows cleaning water to be delivered therethrough or allows delivered cleaning water to be suctioned therethrough.

The fluid supply and discharge port 500 communicates with the cleaning connector 318 provided in the base end surface 302 of the overtube 300 illustrated in FIG. 1 through the fluid passage provided inside the overtube 300 as will be described below. Also, supply (delivery) and suction of cleaning water from the fluid supply and discharge port 500 are performed by the fluid supply and suction device 120 connected to the cleaning connector 318 via the water supply tube 122.

Meanwhile as illustrated in an enlarged perspective of the vicinity of the endoscope delivery port 312 of the endoscope insertion passage 306 in FIG. 13, the endoscope insertion part 102 inserted into the endoscope insertion passage 306 is adapted to be capable of being positioned by positioning means (to be described below) so that the distal end surface 114 thereof is set to a position where the distal end face is stored inside the endoscope insertion passage 306 (inside the through-hole 362), that is, at a positioning position serving as a first position in the forward-backward direction (the direction of the endoscope insertion axis 306a) that is determined in advance within the endoscope insertion passage 306.

Figure 14:
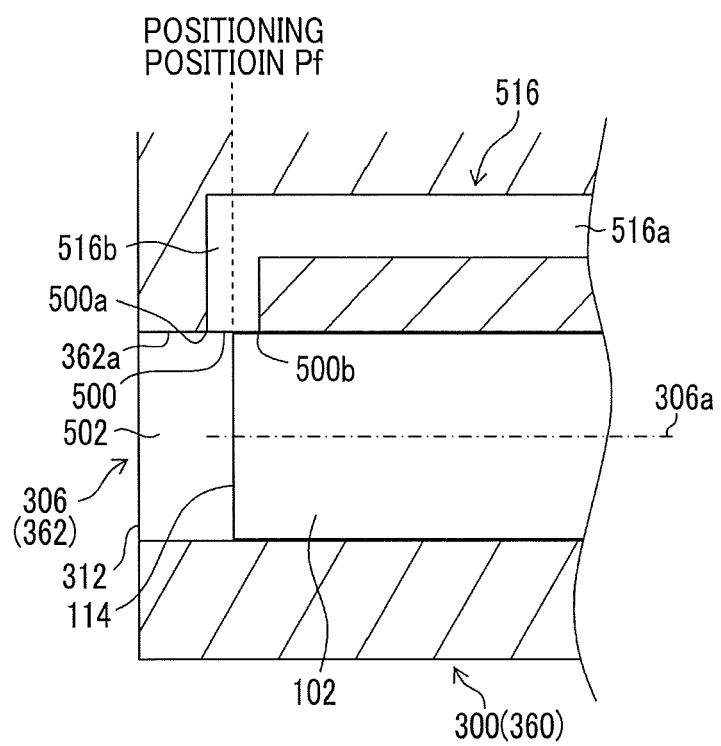
FIG. 14 is a schematic cross-sectional view obtained by cutting the vicinity of the endoscope delivery port of an endoscope insertion passage in a plane including an endoscope insertion axis.

FIG. 14 is a schematic view illustrating a section obtained by cutting the vicinity of the endoscope delivery port 312 of the endoscope insertion passage 306 in a plane including the endoscope insertion axis 306a. As illustrated in this drawing, a positioning position Pf of the distal end surface 114 of the endoscope insertion part 102 is set to a position where a plane including the distal end surface 114 intersects at least the region (the region of the inner wall surface 362a where the fluid supply and discharge port 500 is formed) of the fluid supply and discharge port 500. The positioning position Pf of the distal end surface 114 in the present embodiment is set to a substantial position where the plane including the distal end surface 114 passes through a center position of the fluid supply and discharge port 500, that is, substantially at a substantial center position, in the forward-backward direction, of the region of the fluid supply and discharge port 500.

Additionally, the through-hole 362 that is the endoscope insertion passage 306 has a slightly larger diameter than the external diameter of the endoscope insertion part 102, and has a diameter to such a degree that the endoscope insertion part 102 comes into contact with the inner wall surface 362a or passes therethrough with a minute gap.

Therefore, when the distal end surface 114 of the endoscope insertion part 102 is positioned at the positioning position Pf, a recessed cleaning storage part 502 (recess) that can store a liquid (cleaning water) is formed by the distal end surface 114 of the endoscope insertion part 102 and the inner wall surface 362a in the range from the distal end surface 114 to the endoscope delivery port 312, in the vicinity of the endoscope delivery port 312 of the endoscope insertion passage 306. Also, the fluid supply and discharge port 500 is arranged at a position where this port communicates with the cleaning storage part 502.

According to the above configuration, in a case where foreign matter adheres to the observation window 116 of the distal end surface 114 of the endoscope insertion part 102 inserted through the endoscope insertion passage 306, the cleaning storage part 502 is formed in front of the observation window 116 by positioning the distal end surface 114 of the endoscope insertion part 102 at the positioning position Pf, and a state where cleaning of the observation window 116 is possible without extracting the endoscope insertion part 102 from the endoscope insertion passage 306 is set.

Then, if cleaning water is supplied from the fluid supply and discharge port 500 by the fluid supply and suction device 120 to be described below, the cleaning water is be stored in the cleaning storage part 502. In this case, the foreign matter adhering to the observation window 116 is removed from the observation window 116 due to collision of the cleaning water discharged from the fluid supply and discharge port 500 against the observation window 116 or due to convection caused in the cleaning water stored in the cleaning storage part 502.

If the fluid supply and suction device 120 performs suction from the fluid supply and discharge port 500 after a given amount or more of cleaning water is stored in the cleaning storage part 502, the cleaning water stored in the cleaning storage part 502 is suctioned by the fluid supply and discharge port 500 together with the foreign matter removed from the observation window 116, and is discharged from the fluid supply and discharge port 500. The foreign matter that remains in a state where the foreign mater has adhered to the observation window 116 is removed from the observation window 116 and discharged from the fluid supply and discharge port 500 even by the convection caused in the cleaning storage part 502 in this case. Additionally, since the cleaning storage part 502 is a small space, a suction force from the fluid supply and discharge port 500 is exerted on the entire cleaning storage part 502, and does not cause remaining of droplets in the distal end surface 114 of the endoscope insertion part 102, and the cleaning water including the foreign matter removed from the observation window 116 is completely removed from the cleaning storage part 502.

From the above, the observation window 116 can be cleaned without extracting the endoscope insertion part 102 from the endoscope insertion passage 306.

In addition, in the present embodiment, the distal end surface 114 and the surface of the observation window 116 are arranged on the same plane, and the positioning position Pf is set on the basis of the position of the distal end surface 114 in the forward-backward direction. However, in consideration of also a case where the above surfaces are arranged on different planes, the positioning position Pf may be arranged on the basis of the position of the surface of the observation window 116 in the forward-backward direction instead of being based on the position of the distal end surface 114 in the forward-backward direction. That is, a position where a plane including the observation window 116 of the endoscope insertion part 102 intersects at least the region of the fluid supply and discharge port 500 may be set as the positioning position Pf. Additionally, the positioning position Pf may be set on the basis of a surface, which protrudes forward, out of the distal end surface 114 and the surface of the observation window 116.

Subsequently, the fluid passage for the lens cleaning function, which is formed in the overtube 300, will be described.

Figure 15:
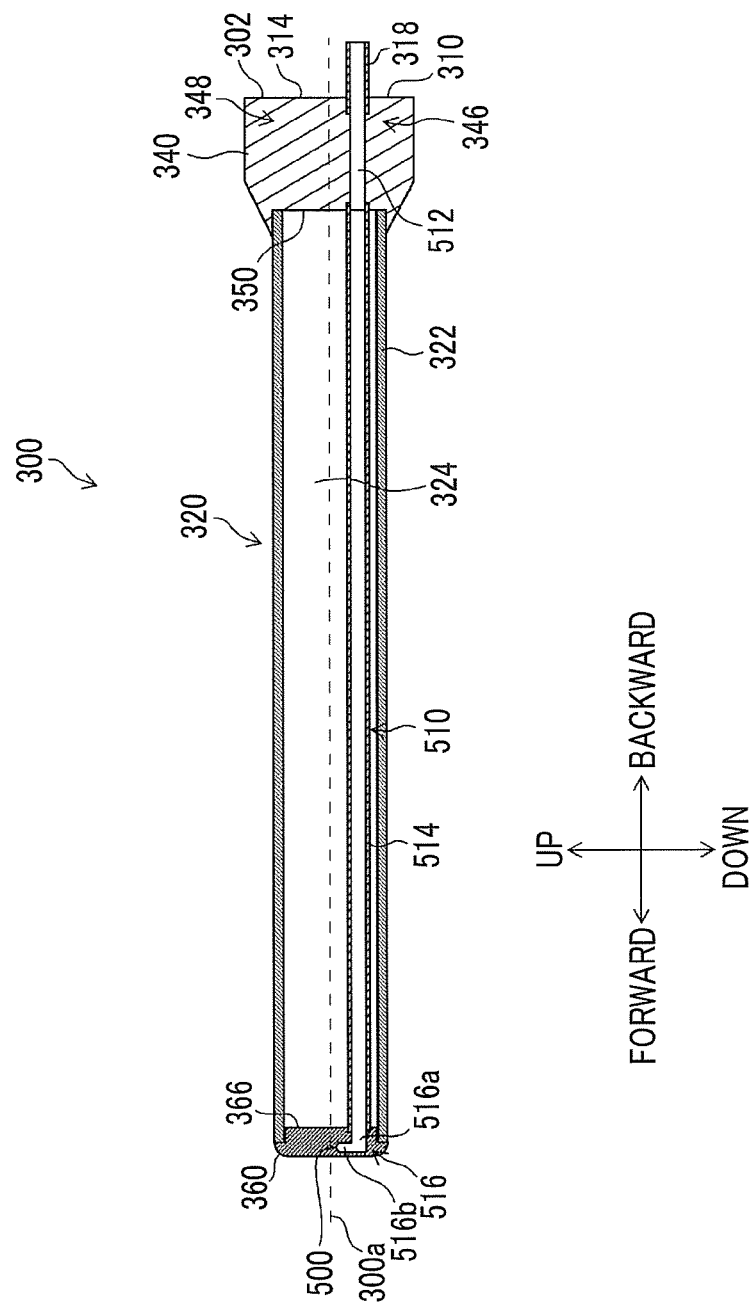
FIG. 15 is a sectional view of the overtube obtained by cutting the overtube in an upward-downward direction along a reference axis.

FIG. 15 is a sectional view of the overtube 300 obtained by cutting the overtube 300 in the upward-downward direction along the reference axis 300a.

The fluid passage 510 for the lens cleaning function is a pipe line that allows the cleaning connector 318 provided in the base end surface 302 of the tubular overtube 300 illustrated also in FIGS. 1 and 3 and the above fluid supply and discharge ports 500 to be communicate with each other inside the overtube 300, and is provided independently from the endoscope insertion passage 306. As illustrated in FIG. 15, the fluid passage 510 is constituted of a through-hole 512 formed in the base end cap 340, an internal pipe line of a liquid delivery tube 514 arranged to be inserted through the overtube body 320 (cavity part 324), and a through-hole 516 formed in the distal end cap 360.

The through-hole 512 of the base end cap 340 is formed to penetrate along the direction of the reference axis 300a from the base end surface 302 to an internal end surface 350 that faces the cavity part 324 of the overtube 300, at a position below the reference axis 300a.

The tubular cleaning connector 318 illustrated also in FIGS. 1 and 3 is provided at a location serving as the end of the through-hole 512 on the base end surface 302 side so as to protrude from and be fixed to the base end surface 302, and the through-hole 512 and the pipe line of the cleaning connector 318 are coupled to each other.

One end (a rear end) of the liquid delivery tube 514 arranged to be inserted through the overtube body 320 is fixed to the internal pipe line of the liquid delivery tube 514, and the through-hole 512 and an internal end surface 350 of the base end cap 340 are coupled to each other.

The liquid delivery tube 514 is linearly formed of, for example, hard materials, and is arranged along the direction of the reference axis 300a so as to be inserted through a space where nothing is arranged within the cavity part 324 that is present below the reference axis 300a (the central axis of the overtube body 320) as illustrated also in FIG. 6.

In addition, in a case where two insertion passages are provided on the left and right with respect to the central axis of the overtube as in the present embodiment, regions that are not effectively used are likely to be generated on an upper side and a lower side with respect to the central axis. Therefore, the fluid passages can be provided without causing an increase in diameter of the overtube if the fluid passages are provided using the regions. In the present embodiment, an increase in diameter of the overtube body 320 does not occur by arranging the liquid delivery tube 514. Additionally, the liquid delivery tube 514 may be a flexible tube.

A front end of the liquid delivery tube 514 is fixed to an internal end surface 366 of the distal end cap 360, and the internal pipe line of the liquid delivery tube 514 and the through-hole 516 formed in the distal end cap 360 are coupled to each other.

The through-hole 516, as illustrated in FIG. 14, is formed from a base end 516a that linearly extends along the direction of the reference axis 300a, and a distal end 516b that is bent substantially at right angles from a distal end of the base end 516a.

The distal end 516b extends toward a direction which intersects the through-hole 362 that constitutes a portion of the endoscope insertion passage 306, and the distal end 516b intersects the through-hole 362 to form the fluid supply and discharge port 500 in the inner wall surface 362a (refer to FIG. 14).

Additionally, a section orthogonal to an axis of the distal end 516b is circular is circular, and the axis of the distal end 516b intersect the endoscope insertion axis 306a at right angles. Therefore, the fluid supply and discharge port 500 becomes a substantially circular opening if strain resulting from the curvature of the inner wall surface 362a is removed. However, in consideration of variations in the positioning position Pf of the distal end surface 114 of the above-described endoscope insertion part 102, the fluid supply and discharge port 500 may has a shape (ellipse or the like) that is long in the forward-backward direction, or the section orthogonal to the axis of the distal end 516b may have a shape (ellipse or the like) that is long in the forward-backward direction.

According to the fluid passage 510 of the above overtube 300, if the fluid supply and suction device 120 is connected to the cleaning connector 318 provided on the base end surface 302 of the overtube 300 via the water supply tube 122 as illustrated in FIG. 1, and cleaning water is delivered from the fluid supply and suction device 120 to the pipe line of the water supply tube 122, the cleaning water is sent into the fluid passage 510 of the overtube 300 via the water supply tube 122 from the cleaning connector 318. The cleaning water sent into the fluid passage 510 flows through the internal pipe line of the through-hole 512 of the base end cap 340, the liquid delivery tube 514 of the overtube body 320, and the through-hole 516 of the distal end cap 360 in order, and is discharged from the fluid supply and discharge port 500.

As described above, in a case where the distal end surface 114 of the endoscope insertion part 102 inserted into the endoscope insertion passage 306 is set to the positioning position Pf and the cleaning storage part 502 is formed at a distal end of the endoscope insertion passage 306, cleaning water is supplied from the fluid supply and discharge port 500 to the cleaning storage part 502, and the cleaning water is stored in the cleaning storage part.

Additionally, if the pipe line of the water supply tube 122 is suctioned by the fluid supply and suction device 120, the suction from the fluid supply and discharge port 500 is performed through the internal pipe line of the through-hole 512 of the base end cap 340, and the liquid delivery tube 514 of the overtube body 320, and the through-hole 516 of the distal end cap 360. In a case where the cleaning storage part 502 is formed at the distal end of the endoscope insertion passage 306 and cleaning water is supplied to that cleaning storage part 502, the cleaning water (also including foreign matter removed from the observation window 116, the same applies below) stored in the cleaning storage part 502 is discharged from the fluid supply and discharge port 500 by this suction.

In addition, although the passage of the above fluid passage 510 in the overtube body 320 is formed by the liquid delivery tube 514 arranged in the cavity part 324 of the overtube body 320, the invention is not limited to this. A pipe line may be formed in the outer wall 322 of the overtube body 320, and the pipe line is may be the passage of the fluid passage 510 in the overtube body 320.

Next, the positioning means for positioning the endoscope insertion part 102 so that the position, in the forward-backward direction, of the distal end surface 114 of the endoscope insertion part 102 coincides with the above-described predetermined positioning position Pf (in the present embodiment, the center position of the fluid supply and discharge port 500) will be described.

First, a positioning mechanism serving as the positioning means of the first embodiment will be described.

Figure 16:
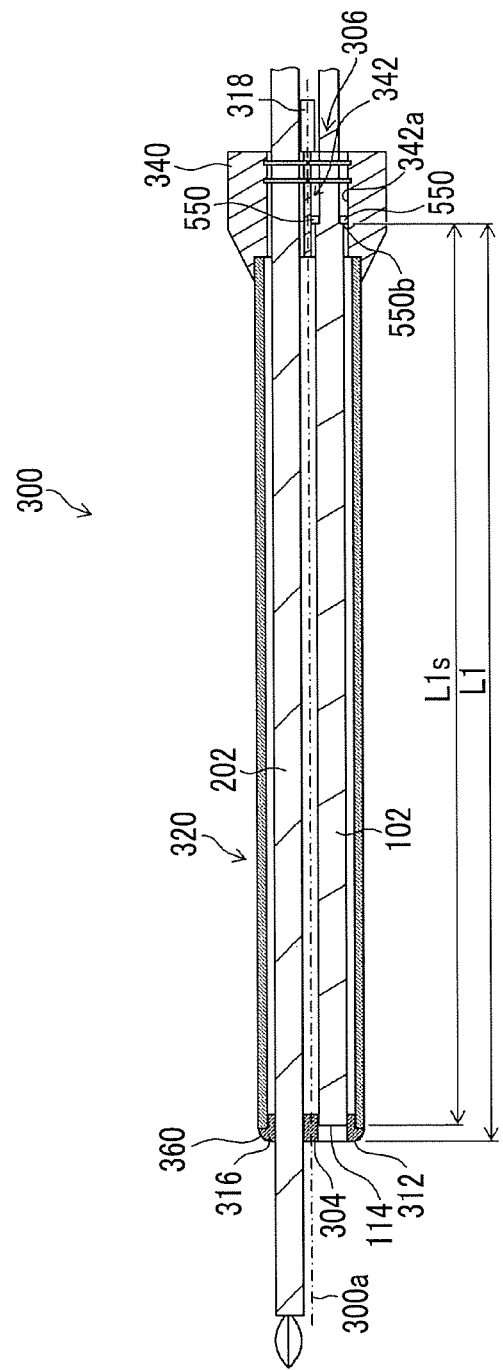
FIG. 16 is a sectional view of the overtube including positioning means of a first embodiment.
Figure 17:
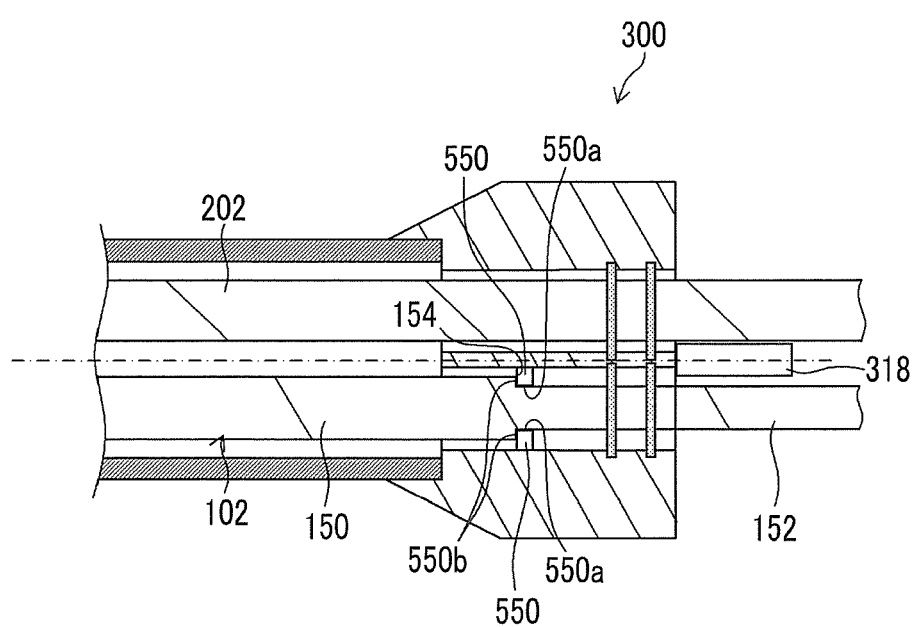
FIG. 17 is an enlarged sectional view illustrating a portion of the base end cap of FIG. 16.

FIG. 16 is a sectional view of the overtube 300 including the positioning means of the first embodiment, and illustrates a state where the endoscope insertion part 102 inserted into the endoscope insertion passage 306 is positioned by the positioning means, and FIG. 17 is an enlarged sectional view illustrating a portion of the base end cap 340 of FIG. 16. In addition, the slider 400 is omitted in FIG. 16.

As illustrated in these drawings, an inner wall surface 342a of the through-hole 342 of the base end cap 340, which is a portion of the endoscope insertion passage 306, is provided with a positioning member 550 (projection) serving as locking means.

The positioning member 550 is formed in an annular shape using elastic members (elastic bodies), such as elastic rubber, and has an insertion hole 550a at a central part thereof. Then, the positioning member 550 is arranged in an annular shape along a circumferential direction of the inner wall surface 342a so as to protrude from the inner wall surface 342a toward the inside (endoscope insertion axis 306a side) by being fixed to the inner wall surface 342a. A stepped part 154 (refer to FIG. 17) formed in the endoscope insertion part 102 is engaged with a front end surface 550b of this positioning member 550.

Here, as illustrated in FIG. 16, the length, in the forward-backward direction, from the front end surface 550b to the endoscope delivery port 312 (that is, distal end surface 304) at the distal end of the overtube 300 is defined as L1. Additionally, the length, in the forward-backward direction, from the front end surface 550b to the positioning position Pf (in the present embodiment, the center position of the fluid supply and discharge port 500) of the distal end surface 114 of the endoscope insertion part 102 is defined as L1s.

In this case, the relationship of at least L1s<L1 is satisfied.

Figure 18:
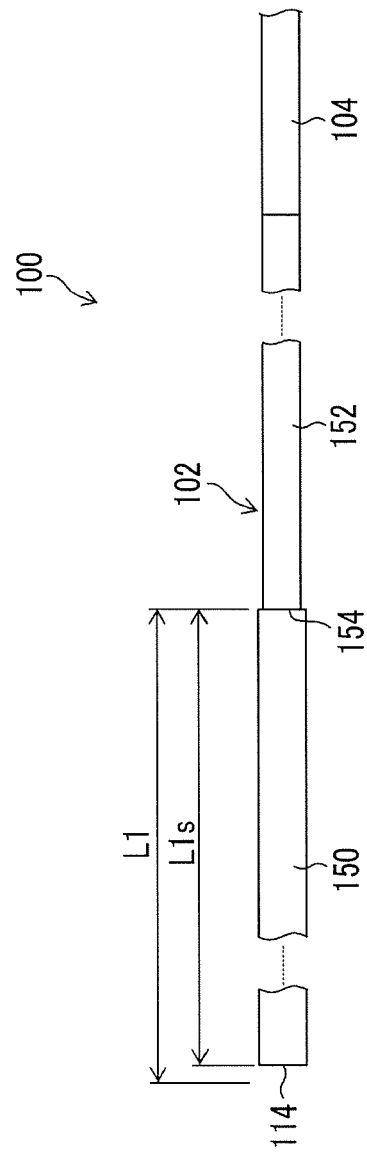
FIG. 18 is a plan view of the endoscope insertion part of an endoscope corresponding to the positioning means of the first embodiment.

FIG. 18 is a plan view of the endoscope insertion part 102 of the endoscope 100 corresponding to the positioning means of the first embodiment.

As illustrated in this drawing, the endoscope insertion part 102 of the endoscope 100 has a larger-diameter part 150 on the distal end side, and a smaller-diameter part 152 closer to the base end side (rear side) than the larger-diameter part, and a stepped part 154 is formed at a boundary between the larger-diameter part 150 and the smaller-diameter part 152.

The larger-diameter part 150 has a diameter of a size such that the larger-diameter part is insertable through the endoscope insertion passage 306 of the overtube 300 and the slider 400 (endoscope-coupled part 420) is capable of being coupled thereto. That is, the larger-diameter part 150 is slightly larger than the internal diameter of the pressure-contact member 426 (refer to FIG. 6 and the like) of the slider 400, and is engageable with the pressure-contact member 426 by frictional engagement.

Additionally, the larger-diameter part 150 has a larger diameter than the diameter of the insertion hole 550a of the positioning member 550 of the endoscope insertion passage 306.

The smaller-diameter part 152 is smaller than at least the larger-diameter part 150, and is insertable through the endoscope insertion passage 306 of the overtube 300. However, since it is not substantially assumed that the endoscope insertion part 102 is inserted into the endoscope insertion passage 306 up to a position where the smaller-diameter part 152 is coupled to the slider 400, the smaller-diameter part 152 may have a diameter of a size such that the smaller-diameter part is capable of being coupled to the slider 400 or may have a diameter of a size such that the smaller-diameter part is not capable of being coupled to the slider 400.

Additionally, the smaller-diameter part 152 has a smaller diameter smaller than the diameter of the insertion hole 550a of the positioning member 550 of the endoscope insertion passage 306, or has a diameter that is substantially coincides with the diameter of the insertion hole 550a.

The stepped part 154 is formed at a boundary position between the larger-diameter part 150 and the smaller-diameter part 152, and has a coupling surface that is an annular surface orthogonal to the axial direction and couples an outer peripheral surface of the larger-diameter part 150 and an outer peripheral surface of the smaller-diameter part 152.

Here, the length of the larger-diameter part 150, that is, the length from the stepped part 154 to the distal end surface 114 coincides with above-described length L1s.

Therefore, as illustrated in FIGS. 16 and 17, the distal end surface 114 of the endoscope insertion part 102 is arranged at the predetermined positioning position Pf (the center position of the fluid supply and discharge port 500) located ahead by the length L1s from the front end surface 550b in a state where the stepped part 154 is made to abut against the front end surface 550b of the positioning member 550 of the endoscope insertion passage 306.

As described above, according to the positioning mechanism serving as the positioning means of the first embodiment, in a case where the endoscope insertion part 102 is inserted through the endoscope insertion passage 306 of the overtube 300, the larger-diameter part 150 of the endoscope insertion part 102 is inserted through the insertion hole 550a by elastically deforming the positioning member 550 of the endoscope insertion passage 306 to increase the diameter of the insertion hole 550a. The smaller-diameter part 160 is inserted through the insertion hole 550a of the positioning member 550 substantially without elastically deforming the positioning member 550 after the larger-diameter part 150 passes through the insertion hole 550a of the positioning member 550.

Additionally, in a state where the endoscope insertion part 102 is delivered from the endoscope delivery port 312, a state where at least the smaller-diameter part 152 is inserted through the insertion hole 550a of the positioning member 550 is brought about.

In a case where the endoscope insertion part 102 is used after being delivered from the endoscope delivery port 312 in this way, a surgeon or another operator moves the endoscope insertion part 102 backward with respect to the overtube 300 when the observation window 116 is cleaned, for example, due to adhesion of foreign matter to the observation window 116. Accordingly, the stepped part 154 of the endoscope insertion part 102, as illustrated in FIGS. 16 and 17, abuts against (engages with) the positioning member 550 (front end surface 550b). In this case, since an operating force required for a backward movement operation of the endoscope insertion part 102 varies rapidly (becomes large), the endoscope insertion part 102 can be stopped in a place where the stepped part 154 of the endoscope insertion part 102 abuts against the positioning member 550, using the variation of the operating force as a guide. Accordingly, the endoscope insertion part 102 can be positioned at a specific position by the positioning member 550.

Meanwhile, in a case where the endoscope insertion part 102 is positioned by the positioning member 550, as illustrated in FIG. 16, the distal end surface 114 of the endoscope insertion part 102 is arranged at the predetermined positioning position Pf (the center position of the fluid supply and discharge port 500) located ahead by the length L1s from the front end surface 550b.

Therefore, the endoscope insertion part 102 can be positioned so that the position, in the forward-backward direction, of the distal end surface 114 of the endoscope insertion part 102 coincides with the predetermined positioning position Pf, and as described above, the cleaning storage part 502 that communicates with the fluid supply and discharge port 500 can be formed at the distal end of the endoscope insertion passage 306.

In addition, in a case where the endoscope insertion part 102 is extracted from the endoscope insertion passage 306 of the overtube 300, a surgeon or another operator performs a further backward movement operation of the endoscope insertion part 102 after it is detected that the stepped part 154 of the endoscope insertion part 102 has abutted against the positioning member 550, so that the positioning member 550 can be elastically deformed and the insertion hole 550a of the positioning member 550 can be inserted through the larger-diameter part 150 and be extracted from the overtube 300.

Additionally, the positioning member 550 may include the function of an airtight valve, and a valve member 346 provided in the vicinity of the endoscope insertion port 310 may also be used as the positioning member.

Additionally, in the endoscope 100 of FIG. 18, the positioning is performed by engaging the positioning member 550 with one stepped part 154 of the endoscope insertion part 102. However, the invention is not limited to this. The positioning may be performed by forming a groove in a circumferential direction in the endoscope insertion part 102 with a constant diameter, and engaging the positioning member 550 with the groove.

Next, a positioning mechanism as the positioning means of the second embodiment will be described.

Figure 19:
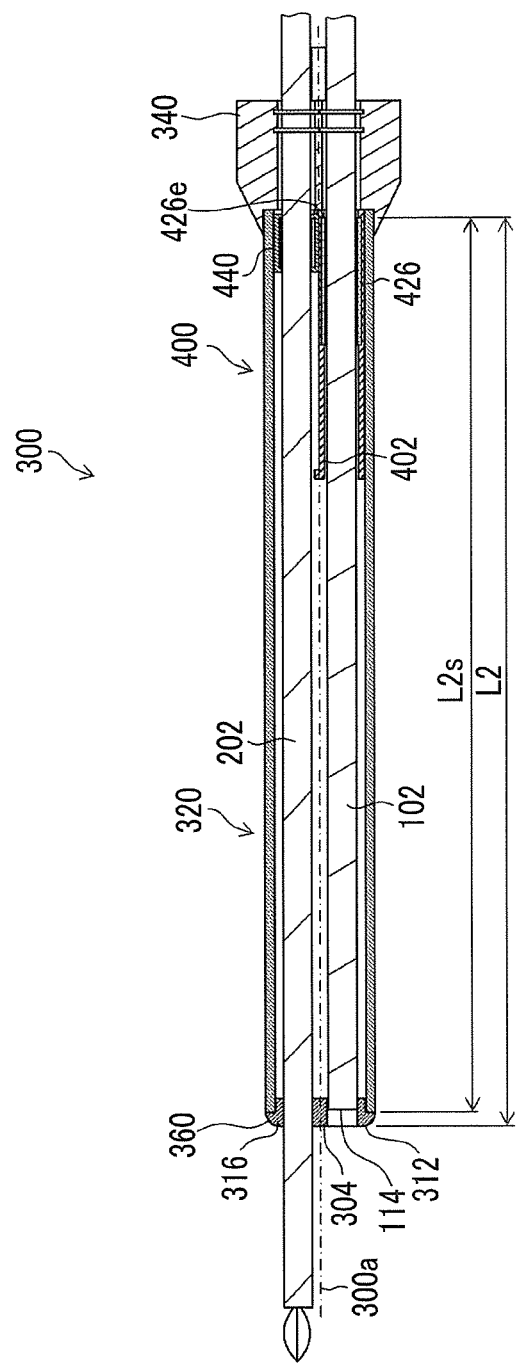
FIG. 19 is a sectional view of the overtube including positioning means of a second embodiment.

FIG. 19 is a sectional view of the overtube 300 including a positioning means of a second embodiment, and illustrates a state where the endoscope insertion part 102 inserted into the endoscope insertion passage 306 is positioned by the positioning means.

In this drawing, the slider body 402 of the slider 400 is arranged at a rear end of a movable range thereof with respect to the overtube body 320. That is, the endoscope insertion part 102 is positioned when the slider body 402 has reached the rear end of the movable range thereof as will be described below.

In this state, regarding the forward-backward direction (the direction of the reference axis 300a), the length, in the forward-backward direction, from the position of a rear end 426e of the pressure-contact member 426 of the slider body 402 to the endoscope delivery port 312 (that is, distal end surface 304) at the distal end of the overtube 300 is defined as L2.

Additionally, the length, in the forward-backward direction, from the position of the rear end 426e of the pressure-contact member 426 to the positioning position Pf (in the present embodiment, the center position of the fluid supply and discharge port 500) of the distal end surface 114 of the endoscope insertion part 102 is defined as L2s.

In this case, the relationship of at least L2s<L2 is satisfied.

Figure 20:
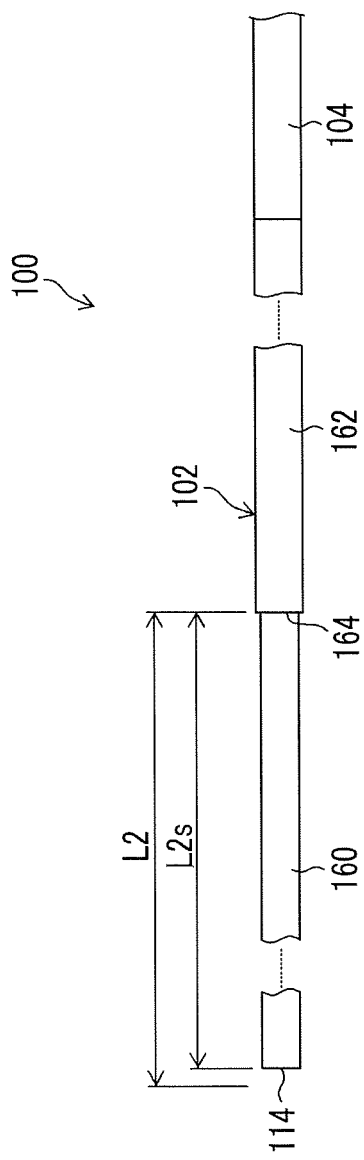
FIG. 20 is a plan view of the endoscope insertion part of the endoscope corresponding to the positioning means of the second embodiment.

Meanwhile, the endoscope insertion part 102 of the endoscope 100 corresponding to the positioning means of the second embodiment is configured as illustrated in a plan view of FIG. 20.

As illustrated in this drawing, the endoscope insertion part 102 of the endoscope 100 has a smaller-diameter part 160 on the distal end side, and a larger-diameter part 162 closer to the base end side (rear side) than the smaller-diameter part, and a stepped part 164 is formed at a boundary between the smaller-diameter part 160 and the larger-diameter part 162.

The smaller-diameter part 160 has a diameter of a size such that the smaller-diameter part is insertable through the endoscope insertion passage 306 of the overtube 300 and is brought into pressure contact with the pressure-contact member 426 (refer to FIG. 6 and the like) of the slider body 402 serving as a sleeve member and the slider body 402 (slider 400) is coupled thereto. That is, the smaller-diameter part 160 is slightly larger than the internal diameter of the pressure-contact member 426, and is engageable with the pressure-contact member 426 through frictional engagement.

The larger-diameter part 162 is larger than the smaller-diameter part 160, and is insertable into the endoscope insertion passage 306 from the position of the endoscope insertion port 310 of the endoscope insertion passage 306 to the position of the rear end 426e of the pressure-contact member 426, but is not insertable thereinto further to a front side than the position of the rear end 426e of the pressure-contact member 426. That is, the larger-diameter part 162 has a diameter that is larger than the internal diameter of the pressure-contact member 426 and makes insertion into the pressure-contact member 426 impossible.

The stepped part 164 is formed at a boundary position between the smaller-diameter part 160 and the larger-diameter part 162, and has a coupling surface that is an annular surface orthogonal to the axial direction and couples an outer peripheral surface of the smaller-diameter part 160 and an outer peripheral surface of the larger-diameter part 162.

Additionally, the movement of the stepped part 164, movement further to the front side than the position of the rear end 426e is restricted when the stepped part abuts against the rear end 426e of the pressure-contact member 426.

Here, the length of the smaller-diameter part 160, that is, the length from the stepped part 164 to the distal end surface 114 coincides with above-described length L2s.

Figure 21:
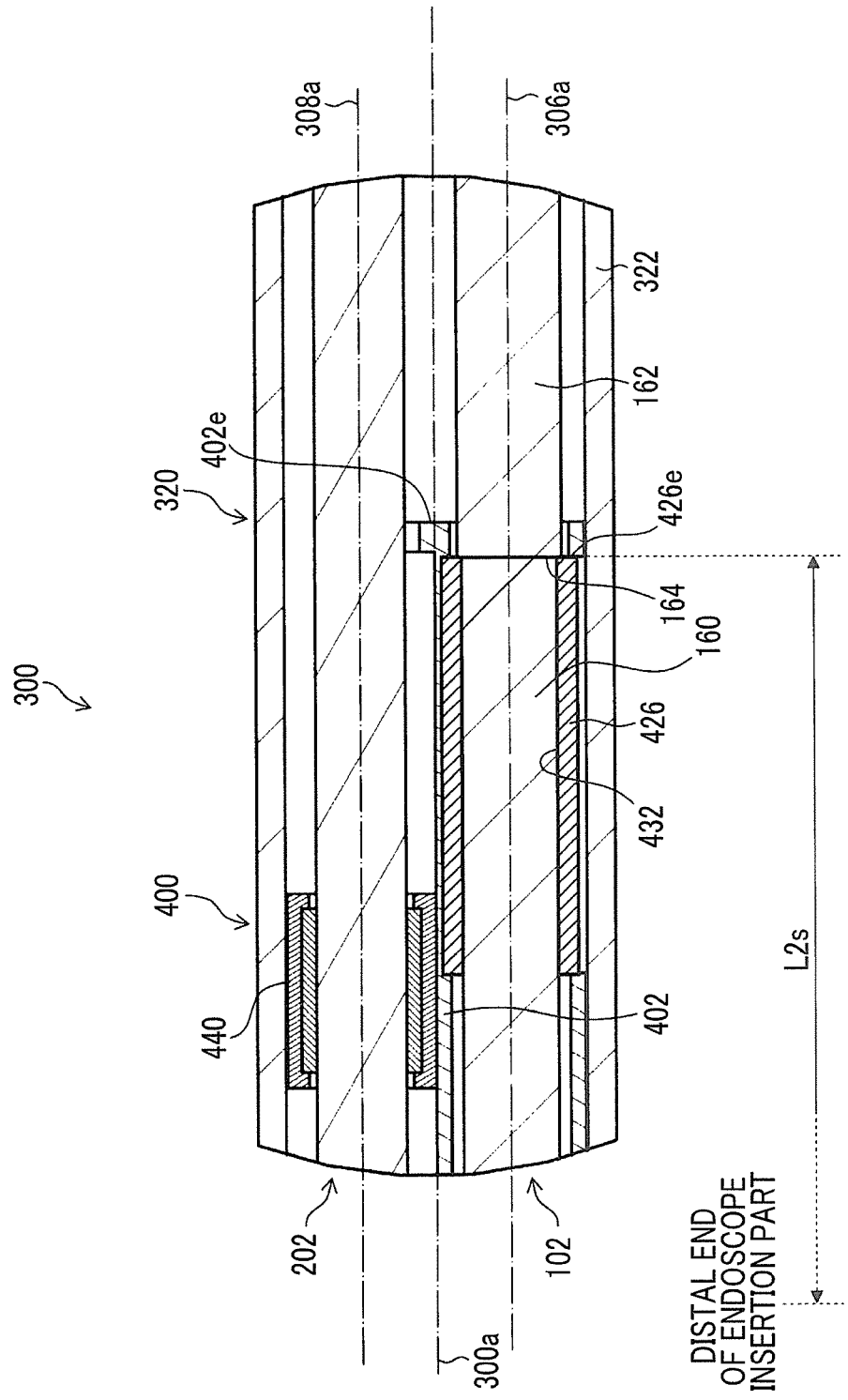
FIG. 21 is an enlarged sectional view illustrating a portion of the overtube, and is a sectional view illustrating a state where the endoscope insertion part of FIG. 20 is coupled to a slider body.

FIG. 21 is an enlarged sectional view illustrating a portion of the overtube 300, and is a sectional view illustrating a state where the endoscope insertion part 102 of FIG. 20 is coupled to the slider body 402.

If the endoscope insertion part 102 is inserted into the endoscope insertion passage 306 of the overtube 300 and the endoscope insertion part 102 is moved forward with respect to the slider body 402 to the maximum extent, as illustrated in this drawing, the stepped part 164 of the endoscope insertion part 102 moves forward up to a position where the stepper part abuts against the rear end 426e of the pressure-contact member 426 of the slider body 402.

Additionally, the smaller-diameter part 160 of the endoscope insertion part 102 is inserted through the through-hole 432 of the pressure-contact member 426 of the slider body 402, and is brought into pressure contact with and engaged with the pressure-contact member 426. That is, the endoscope insertion part 102 is coupled to the slider body 402.

In this case, the length from the position of the rear end 426e of the pressure-contact member 426 to the distal end surface 114 of the endoscope insertion part 102 is equivalent to the length of the smaller-diameter part 160, and becomes the length L2s.

Therefore, if the slider body 402 is set to the position of the rear end of the movable range thereof as illustrated in FIG. 19, the position, in the forward-backward direction, of the distal end surface 114 of the endoscope insertion part 102 is arranged at the predetermined positioning position Pf (the center position of the fluid supply and discharge port 500).

According to the positioning mechanism serving as the positioning means of the above second embodiment, in a case where the endoscope insertion part 102 is inserted through the endoscope insertion passage 306, and the endoscope insertion part 102 is used after being delivered from the endoscope delivery port 312, a surgeon or another operator operates to move the endoscope insertion part 102 forward to the maximum extent with respect to the overtube 300 when the observation window 116 is cleaned, for example, due to adhesion of foreign matter to the observation window 116. Accordingly, the stepped part 164 of the endoscope insertion part 102 is set to the position where the stepped part buts against the rear end 426e of the pressure-contact member 426 of the slider body 402.

Subsequently, the endoscope insertion part 102 or the treatment tool insertion part 202 inserted through the treatment tool insertion passage 308 is operated to move backward, and the slider body 402 is moved to the position of the rear end of the movable range thereof.

Accordingly, the endoscope insertion part 102 can be positioned so that the position, in the forward-backward direction, of the distal end surface 114 of the endoscope insertion part 102 coincides with the predetermined positioning position Pf (the center position of the fluid supply and discharge port 500), and as described above, the cleaning storage part 502 that communicates with the fluid supply and discharge port 500 can be formed at the distal end of the endoscope insertion passage 306.

In addition, in the second embodiment, the stepped part 164 of the endoscope insertion part 102 may be made to abut against (engaged with) the position of the rear end 426e of the pressure-contact member 426. However, the stepped part may be made to abut against (engaged with) portions other than the above position, for example, the position of the rear end surface 402e (refer to FIG. 21) of the slider body 402. In that case, the length of the smaller-diameter part 160 of the endoscope insertion part 102 just has to coincide with the length, in the forward-backward direction, from the abutment position of the slider body 402 in a state where the slider body is set at the rear end of the movable range to the positioning position Pf (the center position of the fluid supply and discharge port 500).

Next, positioning means of a third embodiment will be described.

Figure 22:
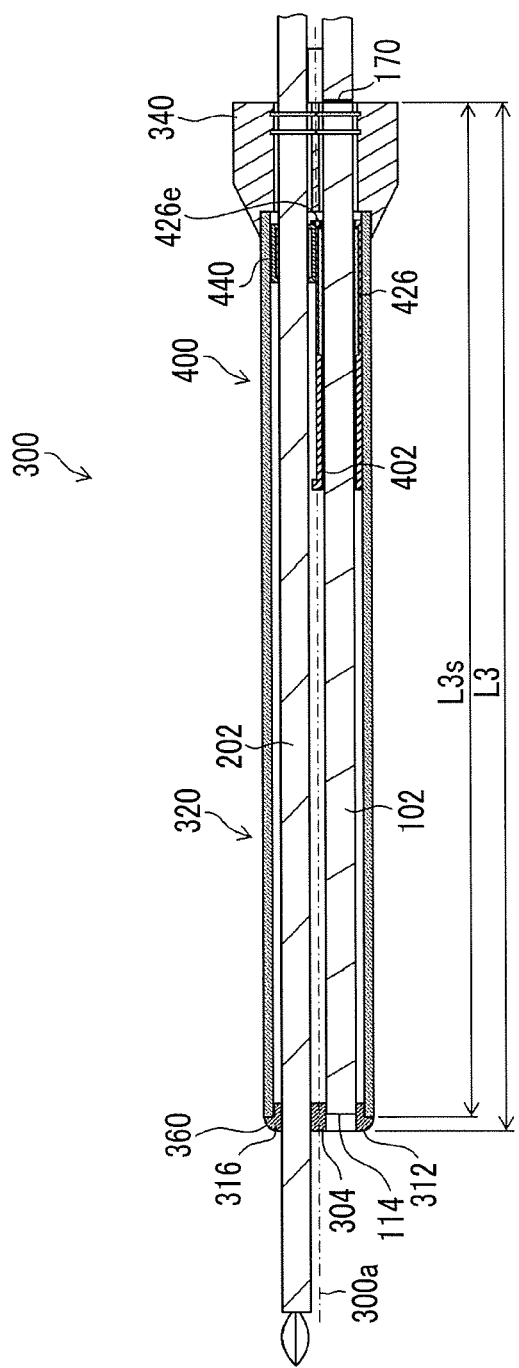
FIG. 22 is a sectional view of the overtube including positioning means of a third embodiment.

FIG. 22 is a sectional view of the endoscope 100 (endoscope insertion part 102) including a positioning part serving as the positioning means of the third embodiment and the overtube 300, and illustrates a state where the endoscope insertion part 102 inserted into the endoscope insertion passage 306 is positioned by the positioning means.

In this drawing, regarding the forward-backward direction (the direction of the reference axis 300a), the length, in the forward-backward direction, from the position (the position of the base end surface 302 of the overtube 300) of the endoscope insertion port 310 of the endoscope insertion passage 306 to the position of the endoscope delivery port 312 (that is, the distal end surface 304) at the distal end of the overtube 300 is defined as L3.

Additionally, the length, in the forward-backward direction, from the position of the endoscope insertion port 310 of the endoscope insertion passage 306 to the positioning position Pf (in the present embodiment, the center position of the fluid supply and discharge port 500) of the distal end surface 114 of the endoscope insertion part 102 is defined as L3s.

In this case, the relationship of at least L3s<L3 is satisfied.

Meanwhile, the endoscope insertion part 102 of the endoscope 100 including the positioning part serving as the positioning means of the third embodiment is provided with an indicator 170 indicating a position apart by the distance L3s from the distal end surface 114 toward the base end side. As a form of the indicator 170, as illustrated in this drawing, a line drawn over one round at the outer periphery of the position of the endoscope insertion part 102 indicated as the indicator 170 may be adopted, or any kinds of form may be adopted as long as a position indicated as the indicator 170 can be recognized.

According to the positioning mechanism serving as the positioning means of the above third embodiment, in a case where the endoscope insertion part 102 is inserted through the endoscope insertion passage 306, and the endoscope insertion part 102 is used after being delivered from the endoscope delivery port 312, a surgeon or another operator operates to move the endoscope insertion part 102 or the treatment tool insertion part 202 inserted through the treatment tool insertion passage 308 back, and makes the position indicated by the indicator 170 provided in the endoscope insertion part 102 coincide with the position of the endoscope insertion port 310 of the base end of the overtube 300 when the observation window 116 is cleaned, for example, due to adhesion of foreign matter to the observation window 116.

Accordingly, the endoscope insertion part 102 can be positioned so that the position, in the forward-backward direction, of the distal end surface 114 of the endoscope insertion part 102 coincides with the predetermined positioning position Pf (the center position of the fluid supply and discharge port 500), and as described above, the cleaning storage part 502 that communicates with the fluid supply and discharge port 500 can be formed at the distal end of the endoscope insertion passage 306.

Figure 13:
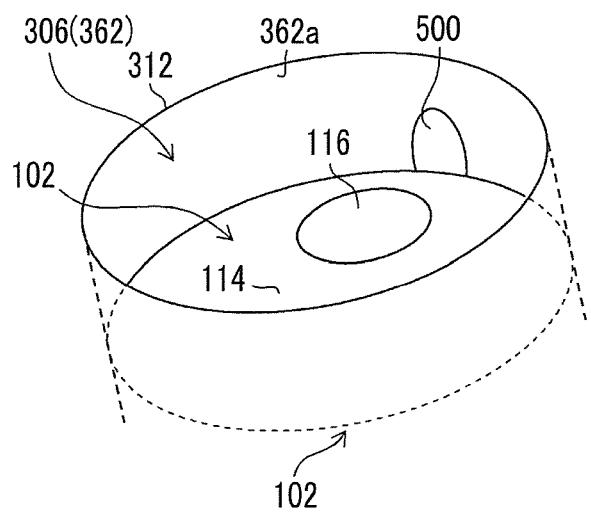
FIG. 13 is an enlarged view of the vicinity of an endoscope delivery port illustrating a state where a distal end surface of the endoscope insertion part is positioned at a positioning position.

In the above, the positioning position Pf of the distal end surface 114 of the endoscope insertion part 102 inserted into the endoscope insertion passage 306, as illustrated in FIGS. 13 and 14 and the like, is the position where the plane including the distal end surface 114 passes through the substantial center position of the fluid supply and discharge port 500. However, at least a form may be adopted in which a position where the distal end surface 114 of the endoscope insertion part 102 equivalent to the distal end of the endoscope insertion part 102 is closer to the base end side than a distal-end-side end 500a (refer to FIG. 14) of the fluid supply and discharge port 500 is the positioning position Pf. That is, the positioning position Pf is satisfactory if supply of cleaning water from the fluid supply and discharge port 500 to the cleaning storage part 502 formed by the distal end surface 114 of the endoscope insertion part 102 and the inner wall surface 362a in the range from the distal end surface 114 to the endoscope delivery port 312 is possible, and the cleaning water stored in the cleaning storage part 502 can be suctioned and discharged from the fluid supply and discharge port 500 without remaining.

Figure 29:
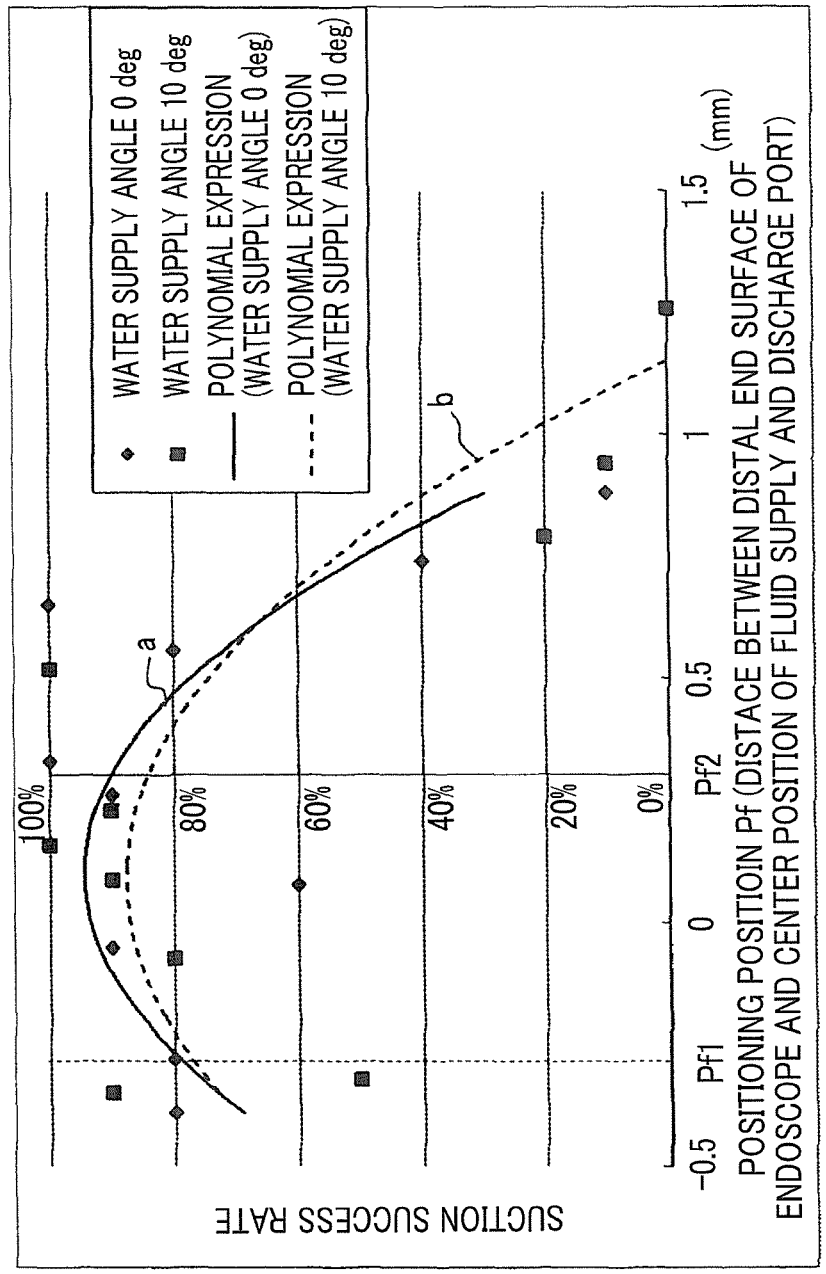
FIG. 29 is a view of experimental results illustrating the suction success rate of cleaning water of the cleaning storage part at different positioning positions of the distal end surfaces of the endoscope insertion part.

FIG. 29 is a graph of experimental results illustrating the number of times when cleaning water could be suctioned without remaining as a suction success rate by actually changing the positioning position Pf to determine whether or not the cleaning water stored in the cleaning storage part 502 could be suctioned (discharged) from the fluid supply and discharge port 500 without remaining at each positioning position Pf and repeating this a predetermined number of times.

In this drawing, the horizontal axis illustrates the distance between the positioning position Pf (the distal end surface 114 set at the positioning position PO and the center position of the fluid supply and discharge port 500 as a positioning position, and illustrates that the positioning position Pf is set closer to the base end side of the endoscope insertion passage 306 as being closer to the right side. A positioning position illustrated by Pf1 in the drawing indicates a position which coincides with the distal-end-side end 500a of the fluid supply and discharge port 500, and a positioning position illustrated by Pf2 in a Fig. illustrates the position which coincides with the base-end-side end 500b (refer to FIG. 14) of the fluid supply and discharge port 500.

Graphs a and b are given by expressing the suction success rate in cases where an angle (water supply angle) at which cleaning water is supplied from the fluid supply and discharge port 500 is 0 degree and 10 degrees with respect to the distal end surface 114, with secondary approximated curves.

As can be seen from this drawing, even in any of graphs a and b, an excellent suction success rate of about 80% or more is obtained if the positioning position Pf is at least a position (Pf1–Pf2) within a range from the distal-end-side end 500a of the fluid supply and discharge port 500 to a base-end-side end 500b. Additionally, a sufficiently excellent suction success rate of about 60% or more is obtained if the positioning position Pf is a position within a range from the position Pf2 of the base-end-side end 500b of the fluid supply and discharge port 500 to about the radius of the fluid supply and discharge port 500 toward the base end side. Moreover, a suction success rate of about 40% or more is obtained at a position within a range from the position Pf2 of the base-end-side end 500b to about the diameter of the fluid supply and discharge port 500 toward the base end side.

The suction success rate fluctuates depending on the suction force of the fluid supply and suction device 120 to be connected to the overtube 300, or the like, and can be sufficiently improved more than the suction success rate illustrated in FIG. 29. Therefore, although the results of the suction success rate illustrated in FIG. 29 do not necessarily limit a range that is settable as the positioning position Pf, it can be understood that at least the positioning position Pf of the distal end surface 114 of the endoscope insertion part 102 is not limited to the position where a plane including the distal end surface 114 intersects the fluid supply and discharge port 500.

Additionally, in the above embodiment, as illustrated in FIG. 14, the distal end 516b of the through-hole 516 that is a fluid passage, that is, the distal end 516b provided with the fluid supply and discharge port 500 in the distal end cap 360 of the distal end of the endoscope insertion part 102 is provided such that the axis (longitudinal axis) thereof is orthogonal to the endoscope insertion axis 306a. That is, the distal end 516b corresponds to a form in which the water supply angle of cleaning water from the fluid supply and discharge port 500 becomes 0° with respect to the distal end surface 114 of the endoscope insertion part 102, and a the form in which the suction success rate is illustrated by the graph a of FIG. 29. However, as can be seen that the suction success rate illustrated by the graph b of FIG. 29 is excellent, the water supply angle of cleaning water from the fluid supply and discharge port 500 may not be 0 degree with respect to the distal end surface 114 of the endoscope insertion part 102.

Figure 30:
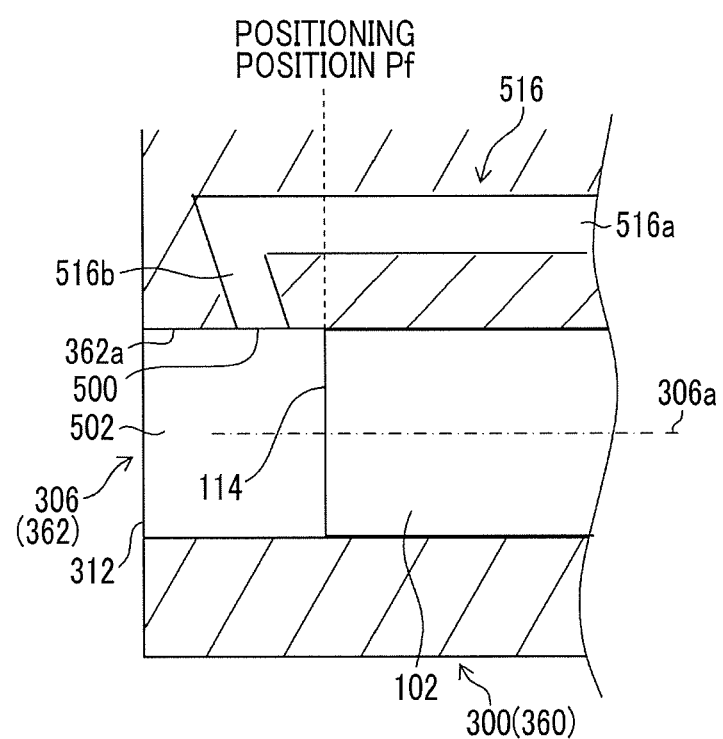
FIG. 30 is a schematic cross-sectional view obtained by cutting the vicinity of the endoscope delivery port of the endoscope insertion passage in the plane including the endoscope insertion axis, and is a view illustrating another embodiment of a fluid passage where a fluid supply and discharge port is provided

For example, as illustrated in FIG. 30, in a case where the positioning position Pf of the distal end surface 114 is a position closer to the base end side rather than the center position of the fluid supply and discharge port 500, the longitudinal axis of the distal end 516b represents an angle that intersects the plane including the distal end surface 114 positioned at the positioning position Pf, and it is preferable that the water supply angle of cleaning water from the fluid supply and discharge port 500 is made larger than 0 degree with respect to the distal end surface 114.

According to this, cleaning water is discharged in a direction directed to the distal end surface 114 from the fluid supply and discharge port 500, and the foreign matter adhering to the observation window 116 is easily removed. Additionally, the above case where the water supply angle is made to be larger than 0 degree with respect to the distal end surface is superior to a case where the water supply angle is made to be 0 degree with respect to the distal end surface 114 in that cleaning water does not remain in the cleaning storage part 502 in the case of suction (discharge) of the cleaning water stored in the cleaning storage part 502 as the positioning position Pf becomes closer to the base end side as illustrated in the graph b of FIG. 29.

Next, an embodiment of the fluid supply and suction device 120 connected to the cleaning connector 318 of the overtube 300 via the water supply tube 122 as illustrated in FIG. 1 will be described. The fluid supply and suction device 120 is a device that performs supply and suction of cleaning water from the fluid supply and discharge port 500 at the distal end of the endoscope insertion passage 306 to the cleaning storage part 502 in order to clean the observation window 116 of the endoscope insertion part 102 inserted through the endoscope insertion passage 306, as described above.

In addition, although the cleaning storage part 502 is formed by setting the distal end surface 114 of the endoscope insertion part 102 inserted into the endoscope insertion passage 306 at the predetermined positioning position Pf using the positioning means as described above, it is supposed that the distal end surface 114 of the endoscope insertion part 102 is set at the positioning position Pf in a case where the cleaning storage part 502 is referred to in the following.

Figure 23:
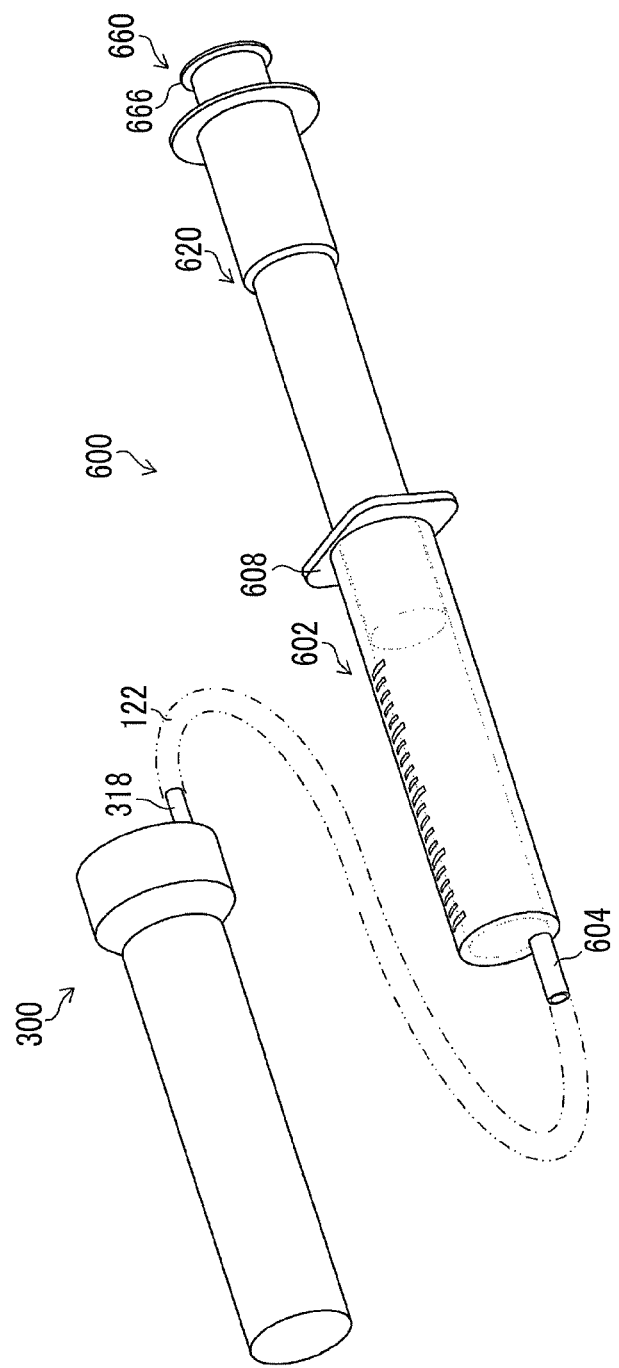
FIG. 23 is a view illustrating an aspect of the connection between the overtube and a syringe device when the syringe device is used as a fluid supply and suction device.

FIG. 23 is a view illustrating an aspect of the connection between the overtube 300 and a syringe device 600 when the syringe device 600 is used as the fluid supply and suction device 120.

As illustrated in this drawing, one end of the water supply tube 122 is fitted to the cleaning connector 318 of the overtube 300, and the other end of the water supply tube 122 is fitted to a nozzle 604 of the syringe device 600. The cleaning connector 318 communicates with the fluid supply and discharge port 500 of the endoscope insertion passage 306 via the fluid passage 510 (refer to FIG. 15 and the like) for the lens cleaning function of the overtube 300 as described above.

The syringe device 600 is configured so that a surgeon or another operator can simply perform delivery and suction of cleaning water from the nozzle 604 with a single hand operation, and the cleaning water can be delivered from the nozzle 604 to the pipe line of the water supply tube 122 by hooking two fingers (for example, the index finger and the middle finger) on a finger-hooking part 608 from the distal end side so as to pinch the syringe body 602, and pressing a finger abutment part 666 of a base end of the plunger rod 660 with a thumb to perform a pushing operation. Accordingly, the cleaning water delivered from the nozzle 604 to the pipe line of the water supply tube 122 is supplied from the fluid supply and discharge port 500 of the endoscope insertion passage 306 through the fluid passage 510 of the overtube 300 to the cleaning storage part 502.

Subsequently, by separating the thumb from the finger abutment part 666 for (pressing is released), the plunger rod 660 can automatically move forward and backward, and can suction the cleaning water in the pipe line of the water supply tube 122 from the nozzle 604. Accordingly, the pipe line of the water supply tube 122 and the fluid passage 510 of the overtube 300 is decompressed, and the cleaning water supplied from the fluid supply and discharge port 500 to the cleaning storage part 502 is suctioned.

Therefore, the operator of the syringe device 600 can perform cleaning of the observation window 116 of the distal end surface 114 of the endoscope insertion part 102 through the operation of only pressing and releasing the finger abutment part 666 of the plunger rod 660.

To describe the configuration of the syringe device 600, the syringe device 600 is constituted of a syringe body 602 having the nozzle 604 formed at a distal end thereof, a plunger body 620 disposed to be inserted into the syringe body 602, and a plunger rod 660 being disposed to be inserted into the plunger body 620 and having the finger abutment part 666 formed at a base end thereof.

Figure 24:
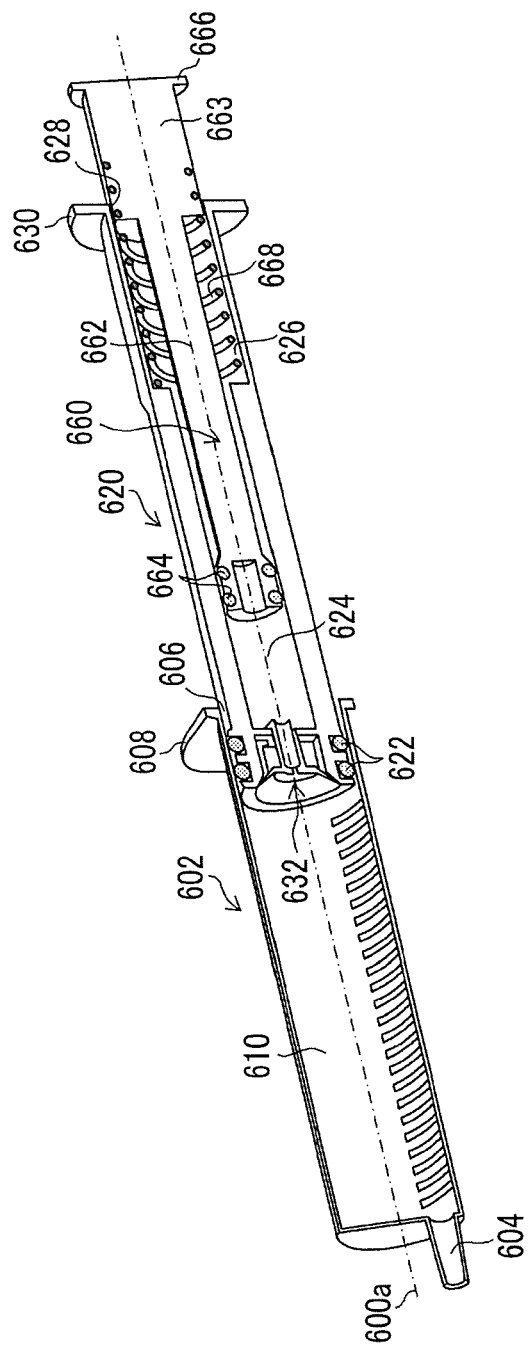
FIG. 24 is a sectional view obtained by cutting the syringe device of FIG. 23 along a central axis.

FIG. 24 is a sectional view obtained by cutting the syringe device 600 along a central axis 600a.

As illustrated in this drawing, the syringe body 602 is formed in a cylindrical shape extending in the direction of the central axis 600a, is blocked on the distal end side, and has an opening 606 on the base end side.

A first space 610 that stores cleaning water is formed inside the syringe body 602.

The first space 610 has some wall surfaces (a side wall surface in columnar shape and a wall surface on the distal end side excluding a wall surface on the base end side) defined by the syringe body 602, and has a wall surface on the base end side defined by a distal end of the plunger body 620 disposed to be inserted thereinto from the opening 606 of the syringe body 602.

Additionally, since the position of the distal end of the plunger body 620 is variable, the volume of the first space 610 is increased or reduced according to the position.

The first space 610 communicates with an exterior space via the pipe line of a tapered nozzle 604 that is formed to protrude from the distal end of the syringe body 602.

Therefore, the first space 610 is allowed to communicate with the fluid supply and discharge port 500, that is, the cleaning storage part 502 of the endoscope insertion passage 306 of the overtube 300 by connecting the nozzle 604 to the cleaning connector 318 of the overtube 300 via the water supply tube 122 as illustrated in FIG. 23.

Additionally, the finger-hooking part 608 on which an operator hooks his/her two fingers (for example, the index finger and the middle finger) pinching syringe body 602 when the operation of the syringe device 600 is performed is formed at a base end of the syringe body 602. The finger-hooking part 608 protrudes in a direction orthogonal to the central axis 600a.

The plunger body 620 is formed in a cylindrical shape extending along the direction of the central axis 600a, the external diameter thereof has a size such that the plunger body is insertable into the syringe body 602 except for the flange part 630 on the base end, and is disposed to be inserted into the syringe body 602.

Two O rings 622 formed of elastic materials are installed on an outer wall surface of the distal end of the plunger body 620. The O rings 622 are slidably brought into close contact with an inner wall surface of the syringe body 602, and block a gap between the inner wall surface of the syringe body 602, and the plunger body 620.

Therefore, if the plunger body 620 is pushed (moved forward and backward) to the distal end side with respect to the syringe body 602, the volume of the first space 610 is reduced, and the cleaning water stored in the first space 610 is delivered from the nozzle 604.

In addition, a position where any one portion of the distal end of the plunger body 620 abuts against any one portion inside the syringe body 602 and further pushing of the plunger body is restricted is a maximum push position of the plunger body 620.

Meanwhile, the second space 624 that stores cleaning water is formed inside the plunger body 620.

The second space 624 has some wall surfaces (a side wall surface in columnar shape and a wall surface on the distal end side excluding a wall surface on the base end side) defined by the plunger body 620, and has a wall surface on the base end side defined by a distal end of the plunger rod 660 disposed to be inserted thereinto from an opening 628 on the base end side of the plunger body 620.

Additionally, since the position of the distal end of the plunger rod 660 is variable, the volume of the second space 624 is increased or reduced according to the position.

The second space 624 communicates with the first space 610 via a check valve member 632 with an orifice provided at the distal end of the plunger body 620.

Although the configuration of the check valve member 632 with an orifice will be described below, the distal end of the plunger body 620 is provided with a first communication passage and a second communication passage that allow the first space 610 and the second space 624 to communicate with each other.

The first communication passage is a communication passage provided with an orifice that restricts the flow (flow rate) of cleaning water between the first space 610 and the second space 624.

The second communication passage is a communication passage provided with a check valve that allows the flow of cleaning water from the second space 624 to the first space 610 and restricts the flow of a fluid from the first space 610 to the second space 624.

Therefore, the second space 624 communicates with the first space 610 through the first communication passage and the second communication passage.

Additionally, a coil spring housing chamber 626 for housing and arranging a coil spring (compression coil spring) fixed to the plunger rod 660 is formed on the base end side inside the plunger body 620. The coil spring housing chamber 626 is made to have a larger diameter than a region on the distal end side where the second space 624 is capable of being formed inside the plunger body 620.

Moreover, the flange part 630 for allowing a finger to be hooked thereon when pulling out the plunger body 620 with respect to the syringe body 602 (for example, when the first space 610 is filled with cleaning water), is formed at the base end of the plunger body 620. The flange part 630 protrudes in the direction orthogonal to the central axis 600*a*.

The plunger rod 660 has a columnar shape extending in the direction of central axis 600*a*, and has a smaller-diameter part 662 formed on the distal end side, and a larger-diameter part 663 formed on the base end side. Additionally, the base end of the plunger rod 660 is provided with the finger abutment part 666 against which an operator presses with his/her thumb when the operation of the syringe device 600 is performed. The finger abutment part 666 protrude in the direction orthogonal to the central axis 600*a*, and a larger circular flat surface than the diameter of the larger-diameter part 663 is formed at the base end of the plunger rod 660.

The smaller-diameter part 662 of the plunger rod 660 has an external diameter such that the smaller-diameter part is insertable up to the distal end inside the plunger body 620, and has two O rings 664 formed of elastic materials installed on an outer peripheral surface of a distal end thereof. The O rings 664 are slidably brought into close contact with an inner wall surface of the plunger body 620, and block a gap between the inner wall surface of the plunger body 620, and the plunger rod 660.

Therefore, if the plunger rod 660 is pushed to (moved forward) the distal end side with respect to the plunger body 620, the volume of the second space 624 is reduced, and the cleaning water stored in the second space 624 is delivered to the first space 610.

In addition, a position where any one portion of the distal end of the plunger rod 660 abuts against any one portion inside the plunger body 620 and further pushing of the plunger rod is restricted is a maximum push position of the plunger rod 660.

The larger-diameter part 663 of the plunger rod 660 has an external diameter such that the larger-diameter part is insertable into the coil spring housing chamber 626 inside the plunger body 620, and a base end of a spiral coil spring 668 (compression coil spring) is fixed to an outer peripheral surface of the larger-diameter part.

The coil spring 668 extends in a range where the coil spring reaches the smaller-diameter part 662 of the plunger rod 660, and is installed in the larger-diameter part 663 so as to surround the smaller-diameter part 662.

The coil spring 668 is arranged to be housed in the coil spring housing chamber 626 of the plunger body 620, and a distal end of the coil spring 668 abuts against a front end portion of the coil spring housing chamber 626 and the position thereof is restricted.

Therefore, if the plunger rod 660 is pushed (moved forward and backward) to the distal end side more than a given amount with respect to the plunger body 620, the coil spring 668 is compressed, and an urging force in a direction in which the plunger rod 660 is moved forward and backward is exerted on the plunger rod 660. That is, the urging force is exerted in the direction in which the volume of the second space 624 is increased. Then, if the plunger rod 660 is released in that state, the plunger rod 660 automatically moves back due to the urging force of the coil spring 668, and the volume of the second space 624 is increased.

In addition, urging means other than coil spring 668 may be used as the urging means for urging the plunger rod 660, and elastic members, such as rubber, may be used.

Here, to describe a series of operations of the syringe body 602, the plunger body 620, and the plunger rod 660, as illustrated in FIG. 24, it is supposed that the plunger body 620 is at a position where the plunger body is pulled out more than the maximum push position with respect to the syringe body 602, and the plunger rod 660 is also at a position where the plunger rod is pulled out more than the maximum push position with respect to the plunger body 620.

In this case, if the index finger and the middle finger are hooked on the finger-hooking part 608 of the syringe body 602 from the distal end side, and the finger abutment part 666 of the plunger rod 660 is pressed with the thumb to perform the pushing operation of the plunger rod 660, first, the plunger rod 660 moves forward to the distal end side with respect to the plunger body 620 against the urging force of the coil spring 668. Additionally, the volume of the second space 624 is reduced.

In this case, the plunger body 620 is stationary with respect to the syringe body 602. That is, the urging force caused by the coil spring 668 is set so as to become smaller than at least the resistance force received when the plunger body 620 moves forward with respect to the syringe body 602.

If the pushing operation of the plunger rod 660 is continued and the pushing operation of the plunger rod 660 is further continued after the plunger rod 660 reaches the maximum push position with respect to the plunger body 620, the plunger body 620 moves forward to the distal end side with respect to the syringe body 602 together with the plunger rod 660. Additionally, the volume of the first space 610 is reduced.

Then, after the plunger body 620 reaches the maximum push position with respect to the syringe body 602 or if the pushing operation of the plunger rod 660 is stopped at the arbitrary positions before the reaching and the thumb is separated from the finger abutment part 666 of the plunger rod 660 to release pressing, the plunger rod 660 automatically moves backward with respect to the plunger body 620 due to the urging force of the coil spring 668, and the volume of the second space 624 is increased.

That is, the urging force of the coil spring 668 when the plunger rod 660 is set at the maximum push position with respect to the plunger body 620 is set so as to become larger than at least the static friction force (the frictional force of the O rings 664) of the plunger rod 660 in the axial direction with respect to the plunger body 620. Therefore, the plunger rod 660 automatically moves backward with respect to the plunger body 620, and stops at a predetermined position due to a decrease in the urging force of the coil spring 668 gradually reduced together with backward movement.

Supposing that the first space 610 and the second space 624 are filled with cleaning water with respect to the series of operation of the syringe bodies 602, the plunger body 620, and the plunger rod 660 as above, when the plunger rod 660 moves forward with respect to the plunger body 620 through the pushing operation of the plunger rod 660, the cleaning water stored in the second space 624 is delivered to the first space 610 together with there being a reduction in volume of the second space 624. Then, the cleaning water stored in the first space 610 is delivered from the nozzle 604 due to a rise in the pressure of the first space 610 accompanying that delivery.

Additionally, when the plunger body 620 moves forward with respect to the syringe body 602 through the pushing operation after the plunger rod 660 reaches the maximum push position, the cleaning water stored in the first space 610 is delivered from the nozzle 604 together with there being a reduction in volume of the first space 610.

On the other hand, when the plunger rod 660 moves backward with respect to the plunger body 620 due to stop (pressing release) of the pushing operation of the plunger rod 660, the pressure of the second space 624 decreases together with an increase in the volume of the second space 624, and the cleaning water stored in the first space 610 is suctioned to the second space 624. Then, suction from the nozzle 604 to the first space 610 is performed due to a decrease in the pressure of the first space 610 accompanying the suction.

Therefore, in a case where the syringe device 600 is used as the fluid supply and suction device 120 of FIG. 1, cleaning of the observation window 116 of the endoscope insertion part 102 inserted through the endoscope insertion passage 306 of the overtube 300 can be simply performed through the single hand operation of the syringe device 600 as described above.

Specifically, the first space 610 and the second space 624 of the syringe device 600 are filled with cleaning water in advance. The filling of the cleaning water is can be performed by releasing the pressing of the plunger rod 660 while dipping the nozzle 604 in the cleaning water stored in a predetermined container and by pulling out the plunger body 620 with respect to the syringe body 602, in a state where the finger abutment part 666 of the plunger rod 660 is pressed to push the plunger body 620 and the plunger rod 660 to their maximum push positions, respectively.

Then, when the cleaning of the observation window 116 of the endoscope insertion part 102 is performed or in advance, the nozzle 604 of the syringe device 600 filled with the cleaning water is connected to the cleaning connector 318 of the overtube 300 by the water supply tube 122 as illustrated in FIG. 23.

Additionally, when the cleaning of the observation window 116 of the endoscope insertion part 102 is performed, the endoscope insertion part 102 inserted through the endoscope insertion passage 306 of the overtube 300 is positioned by the positioning means described in FIGS. 16 to 21 and the like, and the cleaning storage part 502 (refer to FIG. 13 and FIG. 14 grade) that communicates with the fluid supply and discharge port 500 is formed between the distal end surface 114 of the endoscope insertion part 102 and the endoscope delivery port 312.

In this state, a surgeon or another operator hooks his/her index finger and middle finger on the finger-hooking part 608 of the syringe body 602 of the syringe device 600, and presses the finger abutment part 666 of the plunger rod 660 with his/her thumb to perform the pushing operation of the plunger rod 660 as described above. Accordingly, the cleaning water delivered from the nozzle 604 as described above flows through the water supply tube 122 and the fluid passage 510 of the overtube 300, and is supplied from the fluid supply and discharge port 500 to the cleaning storage part 502. Then, the foreign matter adhering to the observation window 116 is removed from the observation window 116 by the collision of the cleaning water against the observation window 116 or the convection of the cleaning water stored in the cleaning storage part 502.

Subsequently, after a given amount of cleaning water is stored in the cleaning storage part 502, the pushing operation of the finger abutment part 666 of the plunger rod 660 is stopped to release pressing (the thumb is separated from the finger abutment part 666). Accordingly, the plunger rod 660 automatically moves backward due to the urging force of the coil spring 668 as described above, and suction from the nozzle 604 is performed. Then, the cleaning water stored in the water supply tube 122 and the liquid passage of the overtube 300 flows toward the syringe device 600, the cleaning water stored in the cleaning storage part 502 is suctioned from the fluid supply and discharge port 500 together with this and is discharged from the cleaning storage part 502.

In addition, the volume of the cleaning water stored in the syringe device 600 is made larger than at least the amount of total of the volume of the pipe line of the water supply tube 122, the volume of the fluid passage 510 of the overtube 300, and the volume of the cleaning storage part 502.

Next, the check valve member 632 with an orifice of the above plunger body 620 will be described. In a case where the nozzle 604 of the syringe device 600, as illustrated in FIG. 23, is connected to the cleaning connector 318 of the overtube 300 by the water supply tube 122 and supply and suction of cleaning water from the fluid supply and discharge port 500 is performed by the syringe device 600, the amount of supply and the amount of suction of cleaning water from the fluid supply and discharge port 500 with respect to changes in the volume of the first space 610 and the second space 624 of the syringe device 600 performs response of a delay system due to the pipe line resistance from the syringe device 600 to the fluid supply and discharge port 500 of the endoscope insertion passage 306.

Therefore, if automatic backward movement of the plunger rod 660 by the coil spring 668 after the pushing operation of the plunger rod 660 is too fast, the backward movement of the plunger rod 660 may stop before suction of cleaning water from the fluid supply and discharge port 500 is performed.

In that case, a possibility that the decrease in the pressure of the first space 610 may be large and the plunger body 620 may move forward with respect to the syringe body 602 so that the volume of the first space 610 is reduced, and consequently, suction from the fluid supply and discharge port 500 may not be normally performed occurs.

In order to prevent such a situation, the distal end of the plunger body 620 in which the communication passage that allows the first space 610 and the second space 624 to communicate with each other is formed is provided with the check valve member 632 with an orifice, and the orifice is arranged in the communication passage by the check valve member 632. The flow rate of the cleaning water suctioned from the first space 610 to the second space 624 is restricted by this orifice. Therefore, the speed of automatic backward movement of the plunger rod 660 by the coil spring 668 can be suppressed, and a suitable suction speed at which the plunger body 620 does not move forward can be obtained.

Meanwhile, simply by providing the orifice in the communication passage between the first space 610 and the second space 624, an operating force required when the pushing operation of the plunger rod 660 (finger abutment part 666) is performed is increased, and the speed of forward movement also becomes slow. Therefore, operability deteriorates. Thus, a communication passage (the second communication passage) separate from the communication passage (the first communication passage) in which the orifice is arranged is provided by the check valve member 632 with an orifice so as not to be influenced by the orifice at the time of the pushing operation of the plunger rod 660 and so that the orifice works effectively at the time of the automatic backward movement of the plunger rod 660 by the coil spring 668, and a check valve is arranged in the second communication passage. This check valve allows the flow of a large flow rate of cleaning water from the second space 624 to the first space 610, and restricts the flow of a large flow rate of cleaning water from the first space 610 to the second space 624. Therefore, deterioration of the operability when the pushing operation of the plunger rod 660 is performed can be eliminated.

Figure 25:
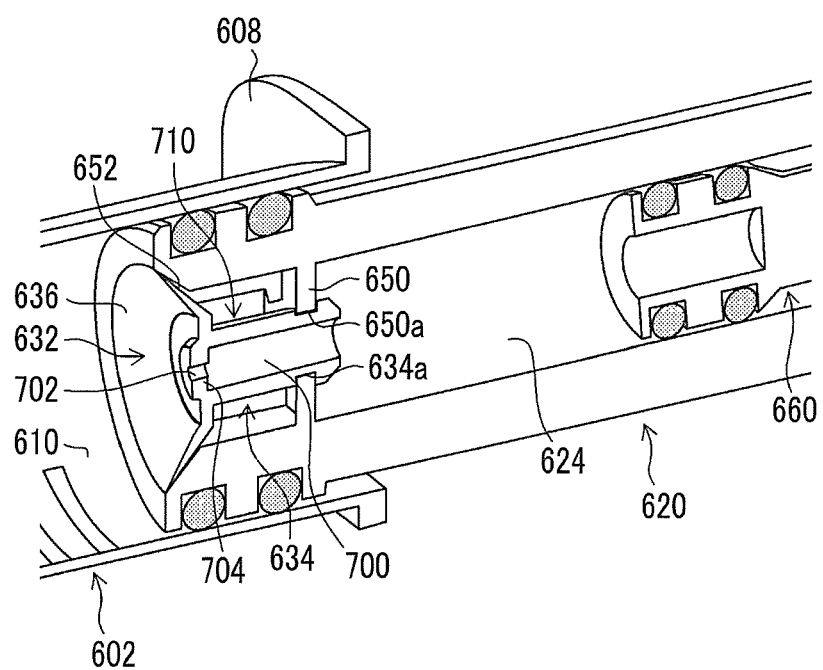
FIG. 25 is an enlarged sectional view illustrating the vicinity of a distal end of a plunger body where a check valve member with an orifice is arranged in the syringe device of FIG. 23.

FIG. 25 is an enlarged sectional view illustrating the vicinity of the distal end of the plunger body 620 where the check valve member 632 with an orifice is arranged. As illustrated in this drawing, the check valve member 632 is integrally formed by an elastic member, and has an orifice part 634 having an orifice 702, and a check valve part 636 that acts as the check valve.

The orifice part 634 is formed in a cylindrical shape, and has an annular groove 634a running in a circumferential direction formed in an outer peripheral surface of a base end thereof. When the groove 634a is engages with a hole 650a formed in a wall 650 of the distal end of the plunger body 620, the entire check valve member 632 is fixed to the distal end of the plunger body 620.

A pipe line 700 that opens to the base end side and communicates with the second space 624 inside the plunger body 620 is formed inside the orifice part 634. A distal end wall 704 that closes the pipe line 700 is formed on a distal end side of the pipe line 700, that is, at a distal end of the orifice part 634, and the orifice 702 that is a small through-hole that allows the communication from the pipe line 700 to the first space 610 inside the syringe body 602 is formed in the distal end wall 704.

Accordingly, the above-described first communication passage which is a communication passage that allows the first space 610 and the second space 624 to communicate with each other and in which the orifice is arranged is formed by the pipe line 700 and the orifice 702 of the orifice part 634 of the check valve member 632. The flow rate of cleaning water that flows through the first communication passage is restricted by the orifice 702.

The check valve part 636 is provided to extend from the distal end of the orifice part 634, and has a shape running a side surface of a truncated cone. That is, the check valve part is formed in a tapered shape that is gradually tapered from the distal end side toward the base end side.

Meanwhile, a pipe line 710 that opens to the distal end of the plunger body 620 and communicates with the first space 610 in a state where the check valve member 632 is detached is formed at the distal end of the plunger body 620. The internal diameter of the pipe line 710 is larger than the external diameter of the orifice part 634, and an inner wall surface 652 of a distal end of the pipe line 710 is formed in a tapered shape that substantially coincides with an outer peripheral surface of the tapered shape of the check valve part 636.

Additionally, the pipe line 710 communicates with the second space 624 via a through-hole (not illustrated) formed in the wall 650 of the orifice part 634, and the first space 610 and the second space 624 communicate with each other via the pipe line 710 in a state where the check valve member 632 is detached.

In contrast, if the check valve member 632 is installed at the distal end of the plunger body 620, the pipe line 710 that communicates with the second space 624 is formed around the orifice part 634. However, when the outer peripheral surface of the check valve part 636 and the inner wall surface 652 of the pipe line 710 come into surface contact with each other, an opening on the distal end side of the pipe line 710 is closed, and the first space 610 and the second space 624 are cut off.

According to this, the flow of cleaning water directed from the second space 624 to the first space 610 acts in a direction in which the outer peripheral surface of the check valve part 636 is separated from the inner wall surface 652 of the pipe line 710, and deforms the check valve part 636. Then, a gap is generated between the outer peripheral surface of the check valve part 636 and the inner wall surface 652 of the pipe line 710. Therefore, the first space 610 and the second space 624 communicate with each other via the pipe line 710 through the gap, and the flow of cleaning water from the second space 624 to the first space 610 is allowed.

According to this, since the flow of cleaning water directed from the first space 610 to the second space 624 acts in a direction in which the outer peripheral surface of the check valve part 636 is brought into pressure contact with the inner wall surface 652 of the pipe line 710, the pipe line 710 is closed and the first space 610 and the second space 624 are cut off. Therefore, the flow of cleaning water from the first space 610 to the second space 624 is restricted.

Accordingly, the above-described second communication passage which is a communication passage that allows the first space 610 and the second space 624 to communicate with each other and in which the check valve is arranged is formed by the pipe line 710 and the check valve part 636 of the check valve member 632. Then, as for the cleaning water that flows through the second communication passage, only the flow thereof from the second space 624 to the first space 610 is allowed by the check valve part 636, and the flow thereof from the first space 610 to the second space 624 is restricted.

As described above, in the configuration of FIG. 23, in a case where the diameter of the fluid passage 510 of the overtube 300 is 1 mm and the length thereof is 150 mm, the diameter of the pipe line of the water supply tube 122 is 2 mm and the length thereof is 1500 mm, and the diameter (the diameter of the endoscope insertion passage 306) of the cleaning storage part 502 formed at the distal end of the endoscope insertion passage 306 is 0.6 mm and the length thereof is 10 mm, a preferable form regarding the dimensions of the following respective parts of the syringe device 600 is obtained on the basis of measured values or the like. Thus, this preferable form will be described. In addition, the length of the water supply tube 122 is 1500 mm also supposing use of operators other than a surgeon.

First, it is desirable that the movable amount (variable amount from the maximum push position) of the automatic backward movement caused by the coil spring 668 of the plunger rod 660 of the syringe device 600 is about 20 mm in consideration of operability.

Figure 26:
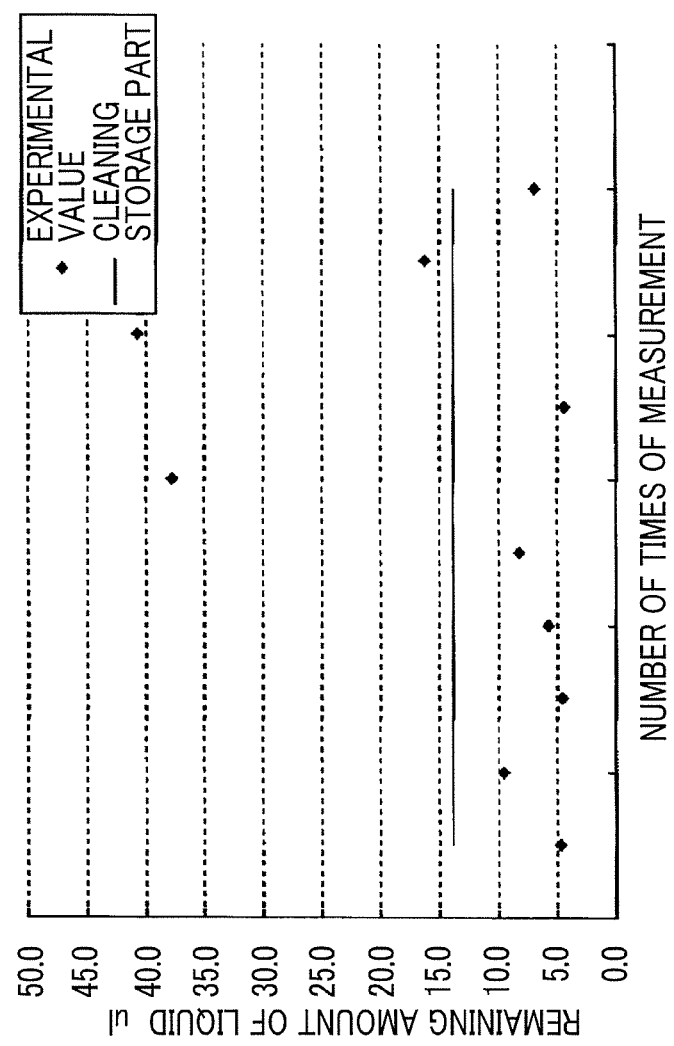
FIG. 26 is a view illustrating data obtained by measuring the amount of cleaning water (the remaining amount of liquid) stored in a cleaning storage part after cleaning water is supplied to the cleaning storage part.

Meanwhile, it is preferable to design the internal diameter (the diameter of the second space 624) of the plunger body 620 so that the volume (a maximum volume variation accompanying the automatic backward movement of the plunger rod 660) of the second space 624 formed by the automatic backward movement of the plunger rod 660 is equal to or more than the volume of the cleaning storage part 502. FIG. 26 illustrates data obtained by measuring the amount of cleaning water (the remaining amount of liquid) stored in the cleaning storage part 502 after cleaning water is supplied to the cleaning storage part 502. If the volume of the cleaning storage part 502 is about 15.0 μL as illustrated in this drawing, it was confirmed that the remaining amount of liquid equal to or more than the volume of the cleaning storage part 502 is generated due to surface tension. Therefore, in order to perform suction so that liquid remaining does not occur in the cleaning storage part 502, it is desirable that at least the volume (the maximum volume variation accompanying the automatic backward movement of the plunger rod 660) of the second space 624 is equal to and more than the volume of the cleaning storage part 502. For example, it is more preferable that the volume of the second space 624 is equal to or more than 0.5 mL.

Figure 27:
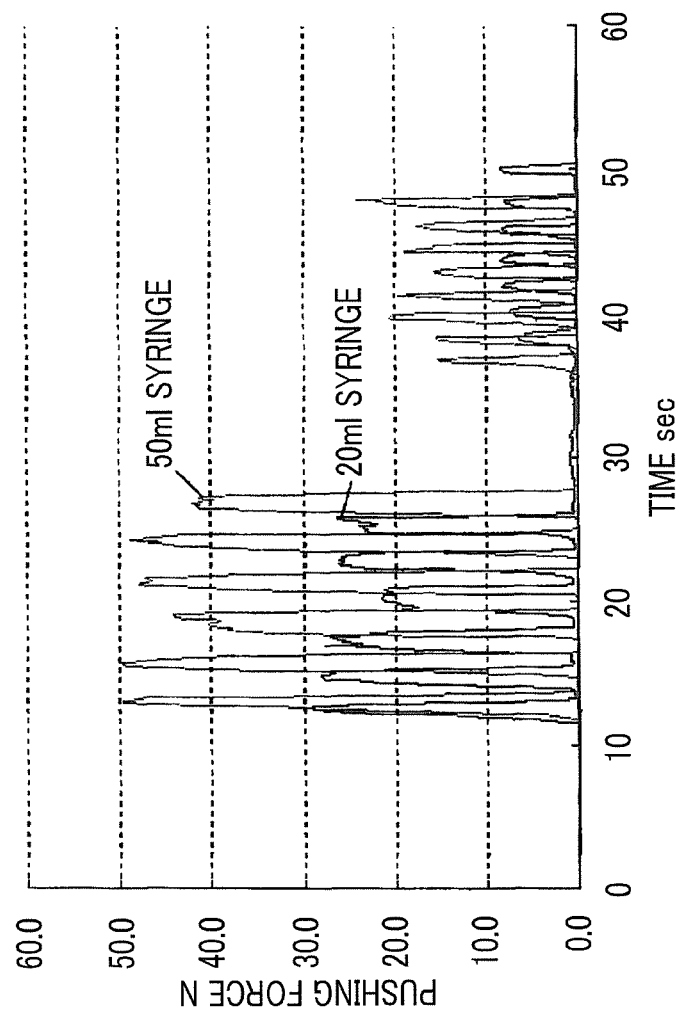
FIG. 27 is a view illustrating results obtained by measuring a pushing force required at the time of the pushing operation of the plunger rod in the syringe device of FIG. 23.

Additionally, although commercial syringe bodies can be used as the syringe body 602 of the syringe device 600, an operating force (pushing force) required for the pushing operation of the plunger rod 660 becomes large in syringe bodies with a large volume. Therefore, operability is not good. For example, as illustrated in FIG. 27, as the result of measuring a pushing force required at the time of the pushing operation of the plunger rod 660 (at the time of the supply of cleaning water to the cleaning storage part 502), the pushing force has a maximum of about 30 N in a 20-mL syringe, whereas the pushing force has a maximum of 50 Ns in a 50-mL syringe. Therefore, it is desirable to use the 20-mL syringe as the syringe body 602.

Figure 28:
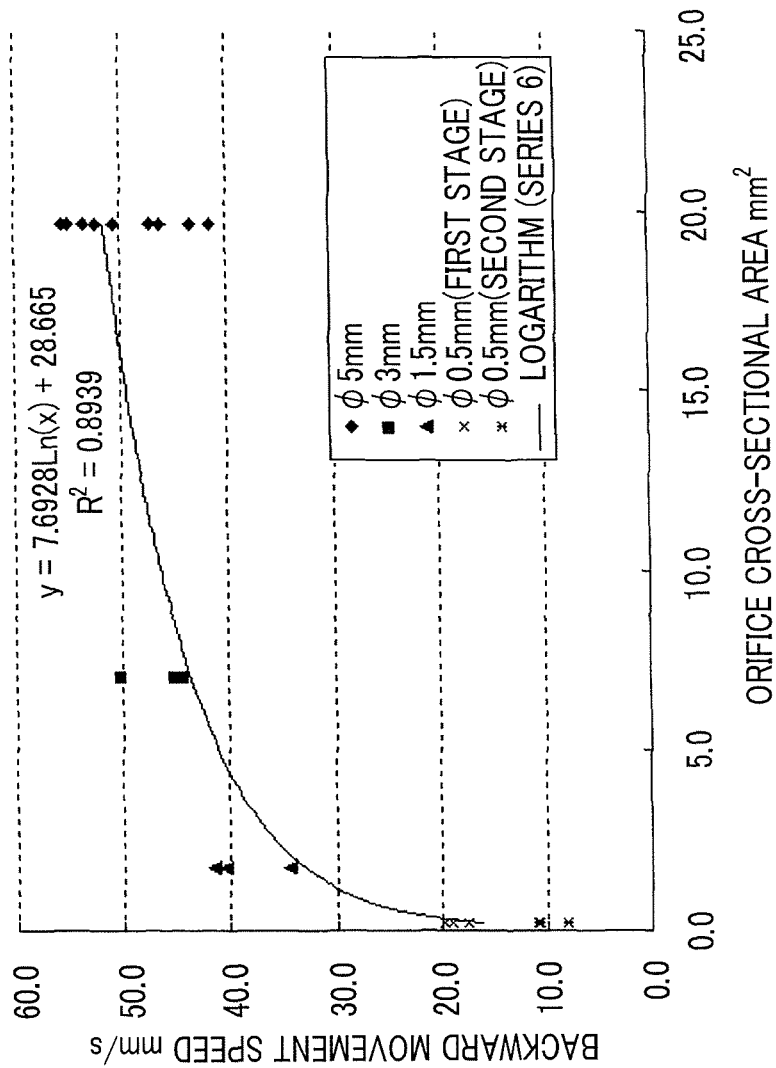
FIG. 28 is a view illustrating data obtained by changing the cross-sectional area (diameter) of an orifice in the syringe device of FIG. 23 to measure the speed of automatic backward movement of the plunger rod.

It is preferable that the orifice 702 in the check valve member 632 of the syringe device 600 has a diameter (orifice diameter) of 1.0 mm or less, and has a length of 1.5 mm. More preferably, the orifice has a diameter of 0.5 mm and a length of 1.5 mm. FIG. 28 illustrates data obtained by changing the cross-sectional area (diameter) of the orifice 702 to measure the speed of the automatic backward movement of the plunger rod 660. According to this, it was confirmed that, as the cross-sectional area (diameter) of the orifice 702 is smaller, the speed of the backward movement of the plunger rod 660 can be made slower, the speed of the automatic backward movement of the plunger rod 660 is equal to or less than 30 mm/s in a diameter of 1.0 mm or less, and a situation in which the plunger body 620 moves forward with respect to the syringe body 602 does not occur. When the orifice 702 has a diameter of 0.5 mm and a length of 1.5 mm, the speed of the automatic backward movement of the plunger rod 660 is about 10 mm/s, and a situation in which the plunger body 620 may move forward with respect to the syringe body 602 is more reliably prevented.

In addition, the fluid supply and suction device 120 may not necessarily be a device like the above-described syringe device 600, and just has to be a device that can perform supply and suction of cleaning water.

As described above, in the above embodiment, a case where the invention is applied to an overtube having the endoscope insertion passage 306 through which the endoscope insertion part 102 is inserted and the treatment tool insertion passage 308 through which the treatment tool insertion part 202 is inserted, and having an interlocking function (slider 400) to move the endoscope insertion part 102 and the treatment tool insertion part 202 forward and backward in an interlocking manner with each other, as the overtube 300 has been described. However, the invention can also be applied to an overtube that does not include the interlocking function, and can also be applied to an overtube that includes only the endoscope insertion passage through which the endoscope insertion part is inserted and does not include the interlocking function.

That is, the invention can be applied to arbitrary overtubes having a cylindrical body having a distal end, a base end, and a longitudinal axis, a distal end opening provided at the distal end of the cylindrical body, a base end opening provided at the base end of the cylindrical body, and an endoscope insertion passage that is provided along a longitudinal axis of the cylindrical body, couples the distal end opening and the base end opening together, and allows an endoscope insertion part to be inserted therethrough so as to be movable forward and backward.

Additionally, in a case where such an overtube is not provided with the interlocking function (slider 400), a sleeve member equivalent to the pressure-contact member 426 of the slider 400 is provided inside the endoscope insertion passage when the positioning means of the second embodiment illustrated in FIGS. 19 to 21 is applied. The sleeve member is fitted to an outer periphery of the endoscope insertion part 102, and moves forward and backward integrally with the endoscope insertion part. The positioning means for positioning the distal end surface 114 (observation window 116) of the endoscope insertion part 102 at a predetermined positioning position includes locking means for locking the endoscope insertion part to the cylindrical body, by directly or indirectly striking the sleeve member against a projection formed in the endoscope insertion passage when the endoscope insertion part moves to the base end side along the a longitudinal axis with respect to the overtube (cylindrical body).

EXPLANATION OF REFERENCES

Pf: positioning position
10: endoscopic surgical device
100: endoscope
102: endoscope insertion part
104: cable part
108: processor device
110: light source device
112: monitor
114, 304: distal end surface
116: observation window
118: illumination window
120: fluid supply and suction device
122: water supply tube
170: indicator
200: treatment tool
202: treatment tool insertion part
204: operating part
206: treatment part
300: overtube
300*a*: reference axis
302: base end surface
306: endoscope insertion passage
306*a*: endoscope insertion axis
308: treatment tool insertion passage
308*a*: treatment tool insertion axis
310: endoscope insertion port
312: endoscope delivery port
314: treatment tool insertion port
316: treatment tool delivery port
318: cleaning connector
320: overtube body
322: outer wall
324: cavity part
340: base end cap
360: distal end cap
400: slider
402: slider body
420: endoscope-coupled part
422: treatment tool-coupled part
426, 446: pressure-contact member
426*e*: rear end
440: sleeve
444: sleeve body
500: fluid supply and discharge port
502: cleaning storage part
510: fluid passage
514: liquid delivery pipe
550: positioning member
550*a*: insertion hole
550*b*: front end surface
600: syringe device
600*a*: central axis
602: syringe body
604: nozzle
608: finger-hooking part
610: first space
620: plunger body
624: second space
626: coil spring housing chamber
630: flange part
632: check valve member
634: orifice part
636: check valve part
650*a*: hole
660: plunger rod
666: finger abutment part
668: coil spring
702: orifice

What is claimed is:

1. An overtube comprising:
   a cylindrical body having a distal end, a base end, and a longitudinal axis;
   a distal end opening provided at the distal end of the cylindrical body;
   a base end opening provided at the base end of the cylindrical body;
   an endoscope insertion passage that is provided along the longitudinal axis of the cylindrical body, couples the distal end opening and the base end opening together, and allows an endoscope insertion part to be inserted therethrough so as to be movable forward and backward;
   a fluid passage having a fluid supply and discharge port and a base-end-side connection port, wherein the fluid supply and discharge port is arranged in an inner wall surface of the endoscope insertion passage and opens to an inside of the endoscope insertion passage on a distal-end-side of the endoscope insertion passage, and the base-end-side connection port connects to a fluid supply/suction device that supplies and suctions a fluid; and
   a pressure-contact member that positions a distal end of the endoscope insertion part at a first position closer to a base end side of the cylindrical body than a distal-end-side end of the fluid supply and discharge port,
   wherein the pressure-contact member includes a locking part having a projection provided in the endoscope insertion passage for locking the endoscope insertion part to the cylindrical body when the endoscope insertion part moves to the base end side of the cylindrical body along the longitudinal axis of the cylindrical body.

2. The overtube according to claim 1,
   wherein the first position is a position where a plane including the distal end of the endoscope insertion part intersects the fluid supply and discharge port.

3. The overtube according to claim 1,
   wherein the fluid supply and discharge port is provided in the fluid passage having a longitudinal axis that intersects a plane including the distal end of the endoscope insertion part positioned at the first position by the pressure-contact member.

4. The overtube according to claim 1,
   wherein the fluid passage is provided independently from the endoscope insertion passage.

5. The overtube according to claim 1,
wherein the endoscope insertion part is locked to the cylindrical body by striking a step provided in the endoscope insertion part against the projection when the endoscope insertion part moves to the base end side of the cylindrical body along the longitudinal axis of the cylindrical body.

6. The overtube according to claim 1,
wherein a sleeve member that is fitted to an outer periphery of the endoscope insertion part and moves forward and backward integrally with the endoscope insertion part is provided inside the endoscope insertion passage, and
wherein the endoscope insertion part is locked to the cylindrical body by striking the sleeve member fitted to the outer periphery of the endoscope insertion part against the projection when the endoscope insertion part moves to the base end side of the cylindrical body along the longitudinal axis of the cylindrical body.

7. An endoscopic surgical device comprising:
an endoscope including an endoscope insertion part having an observation window arranged at a distal end of the endoscope insertion part;
a cylindrical body having a distal end, a base end, and a longitudinal axis, the cylindrical body including a distal end opening provided at the distal end of the cylindrical body, a base end opening provided at the base end of the cylindrical body, an endoscope insertion passage that is provided along the longitudinal axis of the cylindrical body, couples the distal end opening and the base end opening together, and allows the endoscope insertion part to be inserted therethrough so as to be movable forward and backward, and a fluid passage having a fluid supply and discharge port being arranged in an inner wall surface of the endoscope insertion passage and opening to an inside of the endoscope insertion passage on a distal end side thereof;
a fluid supply/suction device that connecting to a base end side of the fluid passage to provide fluid supply and suction; and
a pressure-contact member that positioning a distal end of the endoscope insertion part at a first position closer to a base end side of the cylindrical body than a distal-end-side end of the fluid supply and discharge port when the endoscope insertion part moves to the base end side of the cylindrical body along the longitudinal axis of the cylindrical body,
wherein the pressure-contact member is a locking part for locking the endoscope insertion part to the cylindrical body when the endoscope insertion part moves to the base end side of the cylindrical body along the longitudinal axis of the cylindrical body.

8. The endoscopic surgical device according to claim 7,
wherein the first position is a position where a plane including the distal end of the endoscope insertion part intersects the fluid supply and discharge port.

9. The endoscopic surgical device according to claim 7,
wherein the fluid supply and discharge port is provided in a fluid passage having a longitudinal axis that intersects a plane including the distal end of the endoscope insertion part.

10. The endoscopic surgical device according to claim 7,
wherein the locking part includes a step provided in the endoscope insertion part and a projection provided in the endoscope insertion passage of the cylindrical body, and at least one of the step and the projection is an elastic body.

* * * * *